(12) United States Patent
Blatcher et al.

(10) Patent No.: US 7,737,126 B2
(45) Date of Patent: Jun. 15, 2010

(54) PURINE DERIVATIVE

(75) Inventors: Philip Blatcher, Stevenage (GB); Richard Peter Charles Cousins, Stevenage (GB); Derek Norman Evans, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 308 days.

(21) Appl. No.: 11/569,406

(22) PCT Filed: May 23, 2005

(86) PCT No.: PCT/EP2005/005651

§ 371 (c)(1), (2), (4) Date: Nov. 20, 2006

(87) PCT Pub. No.: WO2005/116037

PCT Pub. Date: Dec. 8, 2005

(65) Prior Publication Data

US 2008/0132526 A1     Jun. 5, 2008

(30) Foreign Application Priority Data

May 24, 2004 (GB) ................................. 0411563.0
May 10, 2005 (GB) ................................. 0509521.1

(51) Int. Cl.
*A61K 31/70* (2006.01)
*C07H 19/167* (2006.01)
(52) U.S. Cl. .................... 514/46; 536/27.23; 536/27.61
(58) Field of Classification Search ........................ None
See application file for complete search history.

(56) References Cited

U.S. PATENT DOCUMENTS

| | | | |
|---|---|---|---|
| 3,796,700 A | 3/1974 | Yoshioka et al. |
| 3,864,483 A | 2/1975 | Stein et al. |
| 3,966,917 A | 6/1976 | Prasad et al. |
| 3,983,104 A | 9/1976 | Vorbruggen |
| 4,167,565 A | 9/1979 | Stein et al. |
| 4,663,313 A | 5/1987 | Bristol et al. |
| 4,704,381 A | 11/1987 | Schaumann et al. |
| 4,767,747 A | 8/1988 | Hamilton et al. |
| 4,962,194 A | 10/1990 | Bridges |
| 4,968,697 A | 11/1990 | Hutchison |
| 4,985,409 A | 1/1991 | Yamada et al. |
| 5,023,244 A | 6/1991 | Goto et al. |
| 5,043,325 A | 8/1991 | Olsson et al. |
| 5,106,837 A | 4/1992 | Carson et al. |
| 5,219,839 A | 6/1993 | Bru-Magniez et al. |
| 5,219,840 A | 6/1993 | Gadient et al. |
| 5,280,015 A | 1/1994 | Jacobson et al. |
| 5,364,862 A | 11/1994 | Spada et al. |
| 5,424,297 A | 6/1995 | Rubio et al. |
| 5,646,128 A | 7/1997 | Firestein et al. |
| 6,703,405 B2 | 3/2004 | Hofmeister et al. |
| 6,710,051 B1 | 3/2004 | Trier |

(Continued)

FOREIGN PATENT DOCUMENTS

| | | |
|---|---|---|
| BE | 768925 | 11/1971 |
| CA | 1077931 A1 | 5/1980 |
| CA | 1082695 A1 | 7/1980 |
| DE | 2034785 | 1/1972 |
| DE | 2213180 | 9/1972 |
| DE | 2317770 | 10/1973 |
| DE | 2621470 | 12/1977 |
| EP | 0066918 A1 | 12/1982 |
| EP | 0181128 A2 | 5/1986 |
| EP | 0181129 A2 | 5/1986 |
| EP | 0222330 A2 | 5/1987 |

(Continued)

OTHER PUBLICATIONS

Caddell et al., "Efficient Synthesis of an Adenosine A2A Agonist: Glycosylation of 2-Haloadenines and an N2-Alkyl-6-chloroguanine," Journal of Organic Chemistry, 69(9), 3212-3215 (2004).*
(R) Caddell et al., "Efficient Synthesis of an Adenosine A2A Agonist: Glycosylation of 2-Haloadenines and an N2-Alkyl-6-chloroguanine," Journal of Organic Chemistry, 69(9), 3212-3215 (2004).*

(Continued)

*Primary Examiner*—Lawrence E Crane
(74) *Attorney, Agent, or Firm*—Robert J. Smith

(57) ABSTRACT

A compound of formula (I)

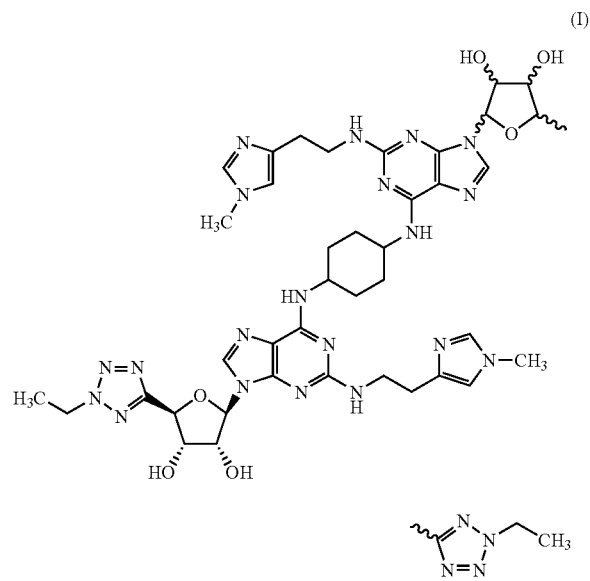

Figure 1:
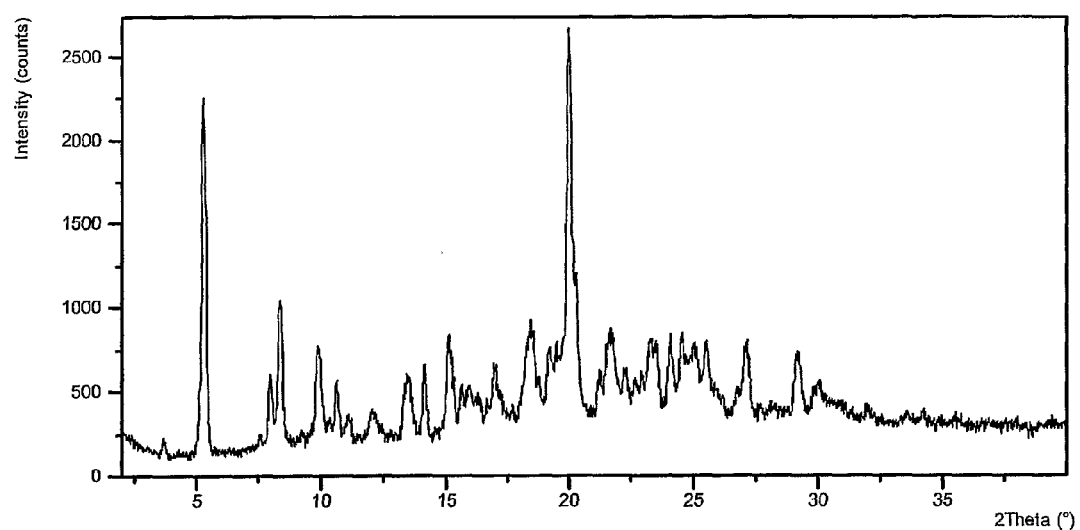

and salts and solvates thereof are disclosed. Compounds of formula (I) are agonists of the adenosine $A2_A$ receptor and are believed to be of potential use in the treatment of inflammatory diseases such as asthma and chronic obstructive pulmonary disease.

56 Claims, 3 Drawing Sheets

U.S. PATENT DOCUMENTS

| | | |
|---|---|---|
| 6,710,086 B1 | 3/2004 | Lai et al. |
| 6,740,655 B2 | 5/2004 | Magee et al. |
| 6,753,322 B2 | 6/2004 | Mantell et al. |
| 6,756,392 B2 | 6/2004 | Magee |
| 6,803,457 B1 | 10/2004 | DeNinno et al. |
| 6,841,549 B1 | 1/2005 | Asano et al. |
| 6,844,362 B2 | 1/2005 | Brown et al. |
| 6,849,629 B2 | 2/2005 | Mylari |
| 6,852,746 B2 | 2/2005 | Silk et al. |
| 2004/0044211 A1 | 3/2004 | Hofmeister et al. |
| 2004/0053953 A1 | 3/2004 | Taveras et al. |
| 2004/0053982 A1 | 3/2004 | Press et al. |
| 2004/0067902 A9 | 4/2004 | Bratzler et al. |
| 2004/0067954 A1 | 4/2004 | Eggenweiler et al. |
| 2004/0077584 A1 | 4/2004 | Mantell et al. |
| 2004/0082578 A1 | 4/2004 | Heintzelman et al. |
| 2004/0106572 A1 | 6/2004 | Fishman et al. |
| 2004/0116376 A1 | 6/2004 | Elzein et al. |
| 2004/0116503 A1 | 6/2004 | Brown et al. |
| 2004/0121978 A1 | 6/2004 | Cristalli |
| 2004/0122045 A1 | 6/2004 | Xu et al. |
| 2004/0127452 A1 | 7/2004 | Van Tilburg et al. |
| 2004/0127510 A1 | 7/2004 | Heintzelman et al. |
| 2004/0132686 A1 | 7/2004 | Van Tilburg et al. |
| 2004/0138175 A1 | 7/2004 | Madge et al. |
| 2004/0142037 A1 | 7/2004 | Engelmayer et al. |
| 2004/0143014 A1 | 7/2004 | Bertrand et al. |
| 2004/0171576 A1 | 9/2004 | Yeadon et al. |
| 2004/0171798 A1 | 9/2004 | Magee et al. |
| 2004/0175382 A1 | 9/2004 | Schafer |
| 2004/0184995 A1 | 9/2004 | Katsuma et al. |
| 2004/0186142 A1 | 9/2004 | Taveras et al. |
| 2004/0198693 A1 | 10/2004 | DeNinno et al. |
| 2004/0204481 A1 | 10/2004 | Fishman |
| 2004/0224975 A1 | 11/2004 | Bailey et al. |
| 2004/0229780 A1 | 11/2004 | Olivera |
| 2004/0229838 A1 | 11/2004 | Mantell et al. |
| 2004/0229904 A1 | 11/2004 | Bunnage et al. |
| 2004/0235774 A1 | 11/2004 | Bratzler et al. |
| 2004/0235833 A1 | 11/2004 | Brown et al. |
| 2004/0248928 A1 | 12/2004 | Downey et al. |
| 2004/0258740 A1 | 12/2004 | Thompson |
| 2004/0259863 A1 | 12/2004 | Eggenweiler et al. |
| 2004/0261190 A1 | 12/2004 | Eggenweiler et al. |
| 2005/0004182 A1 | 1/2005 | Brown et al. |
| 2005/0009864 A1 | 1/2005 | Hofmeister et al. |
| 2005/0014763 A1 | 1/2005 | Brown et al. |
| 2005/0020587 A1 | 1/2005 | Bailey et al. |
| 2005/0020611 A1 | 1/2005 | Barber et al. |
| 2005/0020626 A1 | 1/2005 | Mathias |
| 2005/0020639 A1 | 1/2005 | Smith et al. |
| 2005/0026952 A1 | 2/2005 | Mathias |
| 2005/0032838 A1 | 2/2005 | Bailey et al. |
| 2005/0038033 A1 | 2/2005 | Bunnage et al. |
| 2005/0043326 A1 | 2/2005 | Barber et al. |
| 2005/0059686 A1 | 3/2005 | Eggenweiler et al. |
| 2005/0085437 A1 | 4/2005 | Silk et al. |
| 2005/0085526 A1 | 4/2005 | Brown et al. |

FOREIGN PATENT DOCUMENTS

| | | | |
|---|---|---|---|
| EP | 0232813 A2 | | 8/1987 |
| EP | 0253962 A2 | | 1/1988 |
| EP | 0277917 A2 | | 8/1988 |
| EP | 0139358 A2 | | 11/1988 |
| EP | 0423776 A2 | | 4/1991 |
| EP | 0423777 A2 | | 4/1991 |
| EP | 0496617 A1 | | 7/1992 |
| EP | 0773023 A1 | | 5/1997 |
| EP | 1395287 | | 3/2004 |
| EP | 1396269 A1 | | 3/2004 |
| EP | 1396270 A1 | | 3/2004 |
| EP | 1397140 | | 3/2004 |
| EP | 1400245 A1 | | 3/2004 |
| EP | 1407769 A1 | | 4/2004 |
| EP | 1296996 B1 | | 5/2004 |
| EP | 1252157 B1 | | 6/2004 |
| EP | 1443916 | | 8/2004 |
| EP | 1460064 A1 | | 9/2004 |
| EP | 1466916 A1 | | 10/2004 |
| EP | 1466917 A1 | | 10/2004 |
| EP | 1469864 | | 10/2004 |
| EP | 1477167 A1 | | 11/2004 |
| EP | 1373259 B1 | | 12/2004 |
| EP | 1383515 B1 | | 12/2004 |
| EP | 1486204 A1 | | 12/2004 |
| EP | 1491540 A1 | | 12/2004 |
| EP | 1491541 A1 | | 12/2004 |
| EP | 1229034 B1 | | 4/2005 |
| EP | 1252158 B1 | | 4/2005 |
| EP | 1365776 B1 | | 4/2005 |
| EP | 1414837 | | 10/2005 |
| EP | 1456219 | | 6/2007 |
| GB | 1386656 A | | 2/1972 |
| GB | 2199036 A | | 6/1988 |
| GB | 2203149 A | | 10/1988 |
| JP | 58167599 | | 10/1983 |
| JP | 58174322 | | 10/1983 |
| WO | 8600310 A1 | | 1/1986 |
| WO | 8803147 A1 | | 5/1988 |
| WO | 8803148 A2 | | 5/1988 |
| WO | 9110671 A1 | | 7/1991 |
| WO | 9113082 A1 | | 9/1991 |
| WO | 9205177 A1 | | 4/1992 |
| WO | 9314102 A1 | | 7/1993 |
| WO | 9402497 A1 | | 2/1994 |
| WO | 9417090 A1 | | 8/1994 |
| WO | 9417803 A1 | | 8/1994 |
| WO | 9418215 A1 | | 8/1994 |
| WO | 9502604 A1 | | 1/1995 |
| WO | 9511904 A1 | | 5/1995 |
| WO | 9518817 A1 | | 7/1995 |
| WO | 9602543 A1 | | 2/1996 |
| WO | 9602553 A2 | | 2/1996 |
| WO | 9636729 A1 | | 11/1996 |
| WO | 9740056 A1 | | 10/1997 |
| WO | 9801426 A1 | | 1/1998 |
| WO | 9801459 A1 | | 1/1998 |
| WO | 9816539 A1 | | 4/1998 |
| WO | 9828319 A1 | | 7/1998 |
| WO | 9938877 A2 | | 8/1999 |
| WO | 9941267 A1 | | 8/1999 |
| WO | 9967263 A1 | | 12/1999 |
| WO | 9967264 A1 | | 12/1999 |
| WO | 9967265 A1 | | 12/1999 |
| WO | 00/50011 | | 8/2001 |
| WO | 0157025 A1 | | 8/2001 |
| WO | 0200200 A1 | | 1/2002 |
| WO | 0200676 A1 | | 1/2002 |
| WO | 0236816 A2 | | 5/2002 |
| WO | 0272067 A2 | | 9/2002 |
| WO | 02067909 A1 | | 9/2002 |
| WO | 02070532 A2 | | 9/2002 |
| WO | 02079198 A1 | | 10/2002 |
| WO | 02/094273 A2 | | 11/2002 |
| WO | 02094273 A2 | | 11/2002 |
| WO | 02/096462 A1 | | 12/2002 |
| WO | 02096462 A1 | | 12/2002 |
| WO | 03014137 A1 | | 2/2003 |
| WO | 03029264 A2 | | 4/2003 |
| WO | (L) WO 03/029264 A2 * | | 4/2003 |
| WO | 03/039528 A1 | | 5/2003 |
| WO | 03039528 A1 | | 5/2003 |
| WO | 03048180 A1 | | 6/2003 |

| | | |
|---|---|---|
| WO | 03/061670 A1 | 7/2003 |
| WO | 03061670 A1 | 7/2003 |
| WO | 03062256 A1 | 7/2003 |
| WO | 03/077891 | 9/2003 |
| WO | 03/077891 A1 | 9/2003 |
| WO | 03/082787 | 10/2003 |
| WO | 03080604 A1 | 10/2003 |
| WO | 03080613 A1 | 10/2003 |
| WO | 03088943 A1 | 10/2003 |
| WO | 03/091204 | 11/2003 |
| WO | 03099290 A1 | 12/2003 |
| WO | 2004022071 A1 | 3/2004 |
| WO | 2004022072 A1 | 3/2004 |
| WO | 2004022573 A2 | 3/2004 |
| WO | 2004024180 A1 | 3/2004 |
| WO | 2004028338 A2 | 4/2004 |
| WO | 2004030621 A2 | 4/2004 |
| WO | 2004032921 A1 | 4/2004 |
| WO | 2004033440 A1 | 4/2004 |
| WO | 2004038006 A2 | 5/2004 |
| WO | 2004050040 A2 | 6/2004 |
| WO | 2004052377 A1 | 6/2004 |
| WO | 2004054577 A1 | 7/2004 |
| WO | 2004062671 A2 | 7/2004 |
| WO | 2004076641 A2 | 9/2004 |
| WO | 2004078183 A1 | 9/2004 |
| WO | 2004078184 A1 | 9/2004 |
| WO | 2004079329 A2 | 9/2004 |
| WO | 2004080964 A1 | 9/2004 |
| WO | 2004084800 A2 | 10/2004 |
| WO | 2004091596 A2 | 10/2004 |
| WO | 2004100950 A1 | 11/2004 |
| WO | 2004103998 A1 | 12/2004 |
| WO | 2004108675 A1 | 12/2004 |
| WO | 2004108676 A1 | 12/2004 |
| WO | 2004110454 A1 | 12/2004 |
| WO | 2004112854 A1 | 12/2004 |
| WO | 2005009438 A1 | 2/2005 |
| WO | 2005009964 A1 | 2/2005 |
| WO | 2005009965 A1 | 2/2005 |
| WO | 2005009966 A1 | 2/2005 |
| WO | 2005009989 A1 | 2/2005 |
| WO | 2005009994 A1 | 2/2005 |
| WO | 2005009995 A1 | 2/2005 |
| WO | 2005010001 A1 | 2/2005 |
| WO | 2005012323 A2 | 2/2005 |
| WO | 2005028489 A2 | 3/2005 |

OTHER PUBLICATIONS

Asako et al.; "Leukocyte adherence in rat mesenteric venules: effects of adenosine and methotrexate"; Gastroenterology; 1993; vol. 104; pp. 31-37.
Baker et al.; "5'-substituted-5'-deoxy nucleosides"; Tetrahedron; 1974; vol. 30, No. 16; pp. 2939-2942.
Bedford et al.; "Nonquaternary cholinesterase reactivators. 3. 3(5)-Substituted 1,2,4-oxadiazol-5(3)-aldoximes and 1,2,4-oxadiazole-5(3)-thiocarbohydroximates as reactivators of organophosphonate-inhibited eel and human acetylcholinesterase in vitro"; J. Med. Chem.; 1986; vol. 29, No. 11; pp. 2174-2183.
Burkey et al.; "Adenosine inhibits fMLP-stimulated adherence and superoxide anion generation by human neutrophils at an early step in signal transduction"; Biochem. Biophys. Acta; 1993; vol. 1175, No. 3; pp. 312-318.
CA Listing 210238-44-1; 2009.
CA Listing 252760-70-6, 2009.
CA Listing 252761-70-9, 2009.
Cariello et al.; "Comparison of the computer programs DEREK and TOPKAT to predict bacterial mutagenicity"; Mutagenesis; 2002; vol. 17, No. 4; pp. 321-329.
Castanon et al.; "Functional Coupling of Human Adenosine Receptors to a Ligand-Dependent Reporter Gene System"; Biochem. Biophys. Res. Commun.; 1994; vol. 198, No. 2; pp. 626-631.

Cronstein et al.; "A new physiological function for adenosine: regulation of superoxide anion production"; Trans. Assoc. Am. Physicians; 1983; vol. 96; pp. 384-391.
Cronstein et al.; "Adenosine modulates the generation of superoxide anion by stimulated human neutrophils via interaction with a specific cell surface receptor"; Ann. N.Y. Acad. Sci.; 1985; vol. 451; pp. 291-301.
Cronstein et al.; "Adenosine, an endogenous anti-inflammatory agent", J. Appl. Physiol.; 1994; vol. 76; pp. 5-13.
Cronstein et al.; "The antiinflammatory effects of methotrexate are mediated by adenosine"; Adv. Exp. Med. Biol.; 1994; vol. 370; pp. 411-416.
Cronstein et al.; "The antiinflammatory mechanism of methotrexate. Increased adenosine release at inflamed sites diminishes leukocyte accumulation in an in vivo model of inflammation"; J. Clin. Invest.; 1993; vol. 92; pp. 2675-2682.
Dianzani et al.; "Adenosine modulation of primed human neutrophils"; Eur. J. Pharmacol.; 1994; vol. 263; pp. 223-226.
Elliot et al.; "Interactions of formylmethionyl-leucyl-phenylalanine, adenosine, and phosphodiesterase inhibitors in human monocytes Effects on superoxide release, inositol phosphates and cAMP"; FEBS Letters; 1989; vol. 254, Nos. 1-2; pp. 94-98.
Flora et al.; "Antitumor Activity of Amidoximes (Hydroxyurea Analogs) in Murine Tumor Systems"; Cancer Research; 1978; vol. 38, No. 5; pp. 1291-1295.
Fozard et al.; "Adenosine receptor ligands as potential therapeutics in asthma"; Current Opinion in Investigational Drugs; 2002; vol. 3, No. 1; pp. 69-77.
Green et al.; "Purinergic regulation of bradykinin-induced plasma extravasation and adjuvant-induced arthritis in the rat"; Proc. Natl. Acad. Sci.; 1991; vol. 88, No. 10; pp. 4162-4165.
Hirschorn; "Overview of Biochemical Abnormalities and Molecular Genetics of Adenosine Deaminase Deficiency"; Pediatr. Res.; 1993; vol. 33, No. 4 (Suppl); pp. S35-S41.
Jacobson et al.; "A Novel Pharmacological Approach to Treating Cardiac Ischemia"; J. Biol. Chem.; 2000; vol. 275, No. 39; pp. 30272-30279.
Kohno et al.; "Activation of A3 adenosine receptors on human eosinophils elevates intracellular calcium"; Blood; 1996; vol. 88, No. 9; pp. 3569-3574.
Mester et al.; "Mode of Action of Some Oxidized Sugar Derivatives of Adenine on Platelet Aggregation"; Pathologie-Biologie; 1972; 20 (Suppl.); pp. 11-14.
Peachell et al.; "Inhibition by adenosine of histamine and leukotriene release from human basophils"; Biochem. Pharmacol.; 1989; vol. 38, No. 11; pp. 1717-1725.
Richter; "Effect of adenosine analogues and cAMP-raising agents on TNF-, GM-CSF—, and chemotactic peptide-induced degranulation in single adherent neutrophils"; J. Leukocyte Biol.; 1992; vol. 51, No. 3; pp. 270-275.
Rosengren et al.; "Anti-Inflammatory Effects of an Adenosine Kinase Inhibitor"; J. Immunol.; 1995; vol. 154; pp. 5444-5451.
Sanjar et al.; "TRFK5, an Antibody to Interleukin 5, Selectively Inhibits Antigen-Induced Eosinophil Accumulation in the Guinea-Pig Lung"; Am. Rev. Respir. Dis.; 1992; vol. 145; p. A40.
Schmidt et al.; "Riburonsäurederivate zur gezielten Veränderung der Ribos"; Liebigs. Ann. Chem.; 1974; vol. 1974, No. 11; pp. 1856-1863.
Skubitz et al.; "Endogenous and exogenous adenosine inhibit granulocyte aggregation without altering the associated rise in intracellular calcium concentration"; Blood; 1988; vol. 72, No. 1; pp. 29-33.
Valko et al.; "Fast gradient HPLC method to determine compounds binding to human serum albumin. Relationships with octanol/water and immobilized artificial membrane lipophilicity"; J. Pharm. Sci.; 2003; vol. 92, No. 11; pp. 2236-2248.
Van Schaick et al.; "Hemodynamic effects and histamine release elicited by the selective adenosine A3 receptor agonist 2-CI-IB-MECA in conscious rats"; Eur. J. Pharmacol.; 1996; vol. 308; pp. 311-314.
Wood; "Marker proteins for gene expression"; Current Opinion in Biotechnology; 1995; vol. 6, No. 1; pp. 50-58.

\* cited by examiner

PURINE DERIVATIVE

This application is filed pursuant to 35 U.S.C. § 371 as a United States National Phase Application of International Patent Application Ser. No. PCT/EP2005/005651 filed May 23, 2005, which claim priority from Great Britain Application No. 0411563.0 filed in the United Kingdom on May 24, 2004 and Great Britain Application No. 0509521.1 filed in the United Kingdom on May 10, 2005.

This invention relates to new chemical compounds, processes for their preparation, pharmaceutical formulations containing them and to their use in therapy.

Inflammation is a primary response to tissue injury or microbial invasion and is characterised by leukocyte adhesion to the endothelium, diapedesis and activation within the tissue. Leukocyte activation can result in the generation of toxic oxygen species (such as superoxide anion), and the release of granule products (such as peroxidases and proteases). Circulating leukocytes include neutrophils, eosinophils, basophils, monocytes and lymphocytes. Different forms of inflammation involve different types of infiltrating leukocytes, the particular profile being regulated by the profile of adhesion molecule, cytokine and chemotactic factor expression within the tissue.

The primary function of leukocytes is to defend the host from invading organisms such as bacteria and parasites. Once a tissue is injured or infected a series of events occurs which causes the local recruitment of leukocytes from the circulation into the affected tissue. Leukocyte recruitment is controlled to allow for the orderly destruction and phagocytosis of foreign or dead cells, followed by tissue repair and resolution of the inflammatory infiltrate. However in chronic inflammatory states, recruitment is often inappropriate, resolution is not adequately controlled and the inflammatory reaction causes tissue destruction.

There is evidence from both in vitro and in vivo studies to suggest that compounds active at the adenosine $A_{2A}$ receptor will have anti-inflammatory actions. The area has been reviewed by Cronstein (1994)b. Studies on isolated neutrophils show an $A_2$ receptor-mediated inhibition of superoxide generation, degranulation, aggregation and adherence (Cronstein et al, 1983 and 1985; Burkey and Webster, 1993; Richter, 1992; Skubitz et al, 1988.) When agents selective for the $A_{2A}$ receptor over the $A_{2B}$ receptor (eg CGS21680) have been used, the profile of inhibition appears consistent with an action on the $A_{2A}$ receptor subtype (Dianzani et al, 1994). Adenosine agonists may also down-regulate other classes of leucocytes (Elliot and Leonard, 1989; Peachell et al, 1989). Studies on whole animals have shown the anti-inflammatory effects of methotrexate to be mediated through adenosine and $A_2$ receptor activation (Asako et al, 1993; Cronstein et al, 1993 and 1994). Adenosine itself, and compounds that raise circulating levels of adenosine also show anti-inflammatory effects in vivo (Green et al, 1991; Rosengren et al, 1995). In addition raised levels of circulating adenosine in man (as a result of adenosine deaminase deficiency) results in immunosuppression (Hirschorn, 1993).

The present invention relates to compounds (and salts and solvates thereof) which inhibit leukocyte recruitment and activation and which are potent agonists of the adenosine $A2_A$ (hereinafter $A_{2A}$) receptor. The compounds therefore may be of potential therapeutic benefit in providing protection from leukocyte-induced tissue damage in diseases where leukocytes are implicated at the site of inflammation. The compounds of the invention may also represent a safer alternative to corticosteroids in the treatment of inflammatory diseases, whose uses may be limited by their side-effect profiles.

Further, the compounds of the invention may show an improved profile over known $A_{2A}$-selective agonists in that they may possess one or more of the following properties:

(I) approximately 100 fold more selective for $A_{2A}$ over the human $A_3$ receptor;

(II) approximately 100 fold more selective for $A_{2A}$ over the human $A_{2B}$ receptor;

(III) approximately 100 fold more selective for $A_{2A}$ over the human $A_1$ receptor;

(IV) greater than approximately 90% binding to human serum albumin; and (V) less pronounced cardiovascular effects, in particular reduced tachycardia.

This profile can be considered of benefit as $A_3$ receptors are also found on leucocytes (e.g. eosinophils) and other inflammatory cells (e.g. mast cells) and activation of these receptors may have pro-inflammatory effects (Kohno et al, 1996; Van Schaick et al 1996). It is even considered that the bronchoconstrictor effects of adenosine in asthmatics may be mediated via the adenosine $A_3$ receptor (Kohno et al, 1996). $A_{2B}$ receptors are also found on mast cells and may thus be implicated in mast cell activation. $A_1$ receptors have a wide tissue distribution and can be found on inter alia heart, adipocytes, respiratory smooth muscle, neutrophils, kidney, hippocampus and cortex. $A_1$ receptor activation may thus cause decreased lipolysis, diuresis and CNS activation (Fozard J. R., McCarthy C, Current Opinion in Investigational Drugs 2002 Vol 3. No. 1 p 69-77). A compound that exhibits greater than approximately 90% binding to human serum albumin, such as about 95% binding or more, may be expected to have an improved side effect profile. For example, such compounds may be expected to have less pronounced cardiac effects such as tachycardia.

Figure 2:
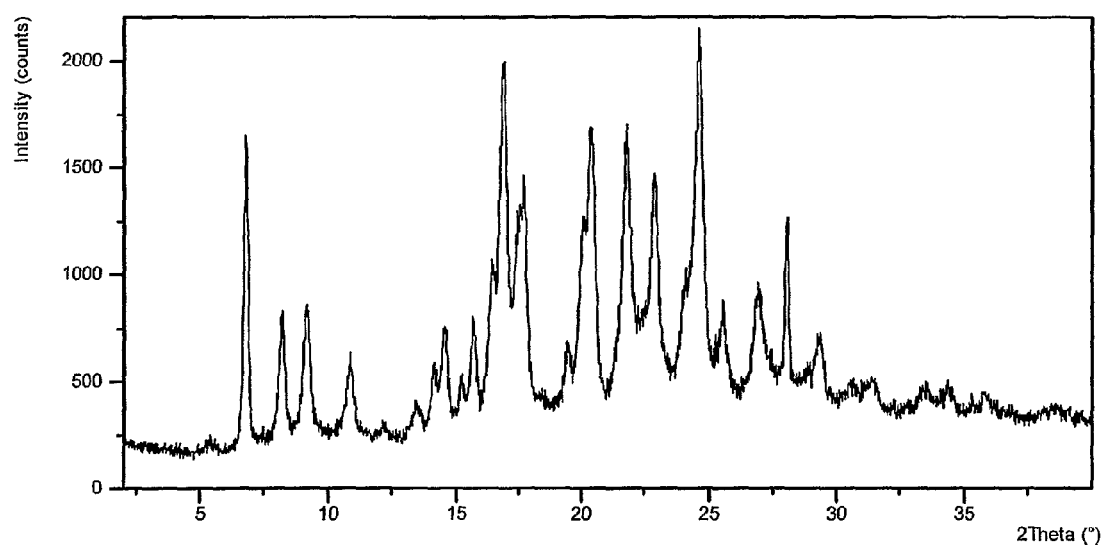
Figure 3:
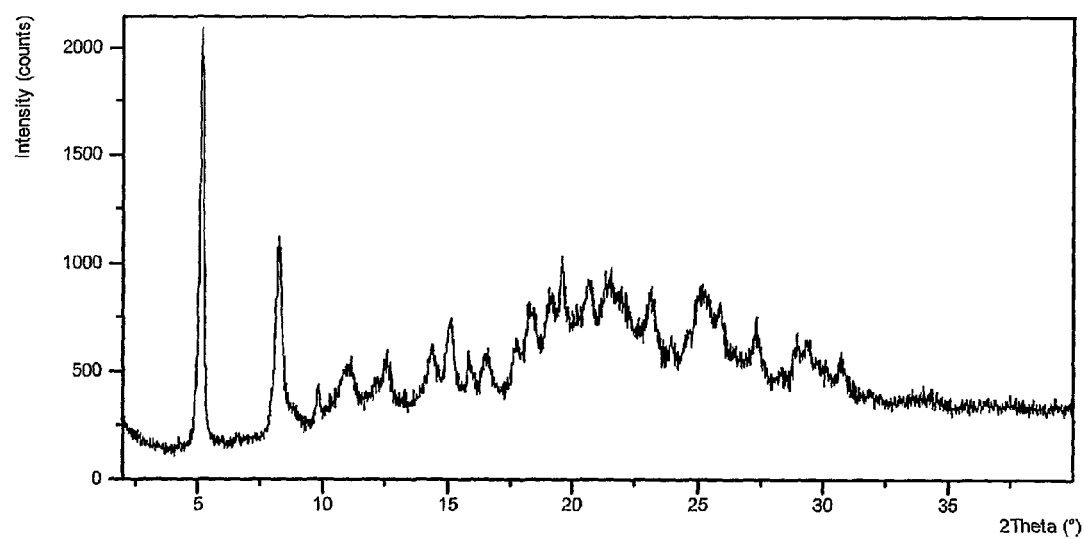

Several drawings are included in the specification, and their brief descriptions are as follows: FIG. 1 illustrates an X-ray pattern diffraction trace of the mono maleate hydrate salt prepared in Example 2. FIG. 2 illustrates an x-ray pattern diffraction trace of the mono terephthalate salt prepared in Example 2. FIG 3. illustrates an X-ray pattern diffraction trace of the mono phthalate salt prepared in Example 2.

According to the invention we provide a compound of formula (I)

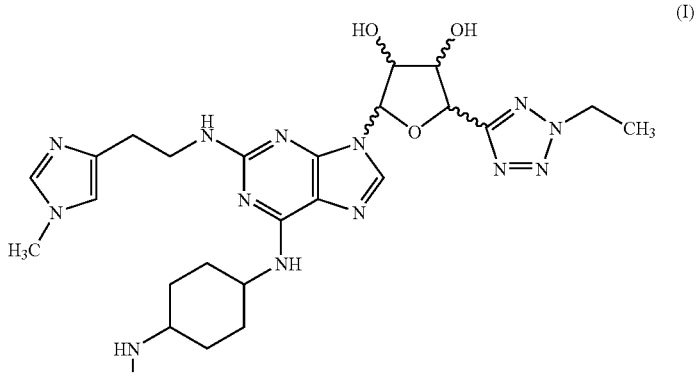

(I)

-continued

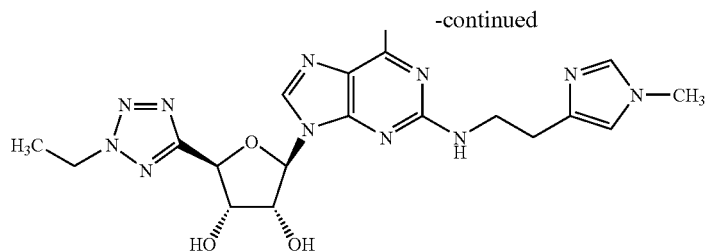

and salts and solvates thereof.

Compounds of formula (I) require absolute stereochemistry about one of the tetrahydrofuran rings such that the stereochemistry about each stereocentre in the tetrahydrofuran ring is as follows:

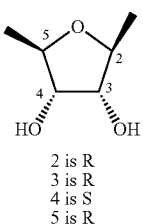

2 is R
3 is R
4 is S
5 is R

However the stereochemistry about each stereocentre in the other tetrahydrofuran ring need not be fixed. Within this requirement the invention encompasses all stereoisomers of the compounds of formula (I) (i.e. diastereoisomers) whether as individual stereoisomers isolated such as to be substantially free of the other stereoisomer (i.e. pure) or as mixtures thereof. An individual stereoisomer isolated such as to be substantially free of the other stereoisomer (i.e. pure) will be isolated such that less than about 10%, for example less than about 1% or less than about 0.1% of the other stereoisomer is present.

Compounds of formula (I) in which the stereochemistry about both of the tetrahydrofuran rings is such that each stereocentre in the tetrahydrofouran ring is fixed as shown above in formula (Ia) are preferred.

Also included within the scope of the invention are all geometric isomers of the compound of formula (I) whether as individual isomers or mixtures thereof. Thus the compound of formula (I) in the trans and cis configuration, in particular trans, forms a further aspect of the invention.

Salts of the compounds of the present invention are also encompassed within the scope of the invention. Because of their potential use in medicine, the salts of the compound of formula (I) are preferably pharmaceutically acceptable salts. Pharmaceutically acceptable salts can include acid addition salts. A pharmaceutically acceptable acid addition salt can be formed by reaction of a compound of formula (I) with a suitable inorganic or organic acid (such as hydrobromic, hydrochloric, formic, sulfuric, nitric, phosphoric, succinic, maleic, terephthalic, phthalic, acetic, fumaric, citric, tartaric, benzoic, p-toluenesulfonic, methanesulfonic or naphthalene-sulfonic acid), optionally in a suitable solvent such as an organic solvent, to give the salt which is usually isolated for example by crystallisation and filtration. Thus, a pharmaceutically acceptable acid addition salt of a compound of formula (I) can be for example a hydrobromide, hydrochloride, formate, sulfate, nitrate, phosphate, succinate, maleate, phthalate, terephthalate, acetate, fumarate, citrate, tartrate, benzoate, p-toluenesulfonate, methanesulfonate or naphthalenesulfonate salt. Other non-pharmaceutically acceptable salts, eg. oxalates or trifluoroacetates, may be used, for example in the isolation of compounds of the invention, and are included within the scope of this invention. The invention includes within its scope all possible stoichiometric and non-stoichiometric forms of the salts of the compounds of formula (I).

Also included within the scope of the invention are all solvates, hydrates, complexes and polymorphic forms of the compound and salts of the invention.

The compounds of formula (I) or protected derivatives thereof may be prepared according to a first process (A) by reacting a compound of formula (II)

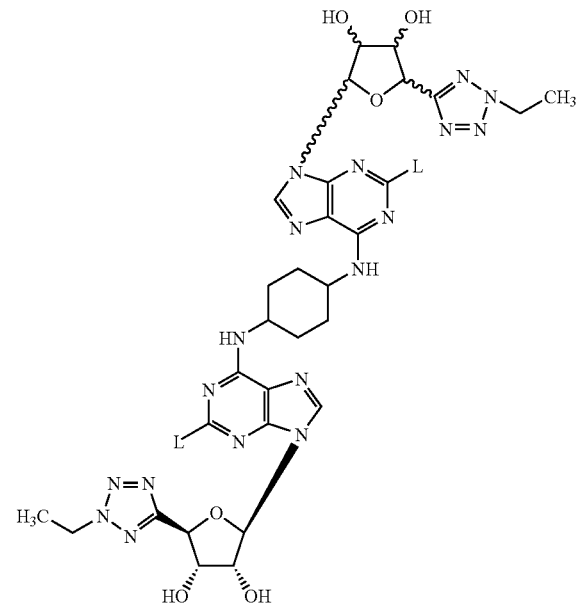

(II)

wherein L represents a leaving group for example halogen particularly chlorine or a protected derivative thereof, with [2-(1-methyl-1H-imidazol-4-yl)ethyl]amine

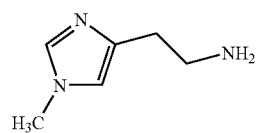

Said reaction will generally involve heating the reagents to a temperature of 50° C. to 150° C., such as 100° C. to 130° C. particularly about 110° C. to 120° C. in the presence of an inert solvent such as DMSO. Alternatively, the reaction can be performed at a lower temperature for example at approximately 100° C. for an extended period such as 18 to 24 hours. The compound of formula (II) may be used in a form in which the hydroxyl groups are protected eg. with acetonide or acetyl groups, particularly acetyl groups.

A compound of formula (II) or a protected derivative thereof may be prepared by reacting a compound of formula (III)

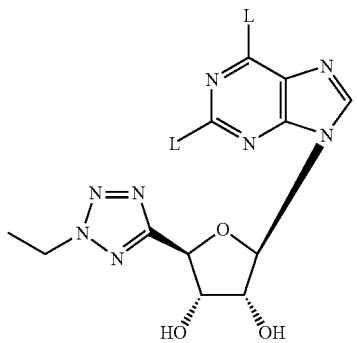
(III)

wherein L represents a leaving group as defined above or a protected derivative thereof, with 1,4-diaminocyclohexane such as trans-1,4-diaminocyclohexane. This reaction will generally be performed in the presence of a base such as an amine base (eg. diisopropylethylamine in a suitable solvent such as an alcohol eg. isopropanol) at an elevated temperature (eg. 50° C. to 60° C.).

A compound of formula (III) or a protected derivative thereof and methods for its preparation is disclosed in WO 98/28319. A compound of formula (III) is intermediate 7 of WO 98/28319. Briefly, a compound of formula (III) may be prepared by reacting a compound of formula (IV)

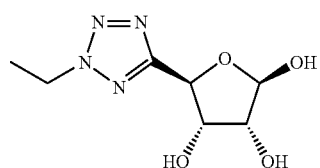
(IV)

or a protected derivative thereof with 2,6-dichloropurine in a suitable solvent under inert conditions in the presence of a Lewis acid such as trimethylsilyl triflate.

Compounds of formula (III) and (IV) may be used in a form in which the hydroxyl groups are protected with suitable protecting groups e.g. with acetonide or acetyl groups, particularly acetyl groups.

Compounds of formula (IV) may be prepared by the methods disclosed in WO98/28319 or by analogous methods. A compound of formula (IV) is Intermediate 6 of WO98/28319.

According to a second process (B), a compound of formula (I) or a protected derivative thereof may be prepared by reacting a compound of formula (V)

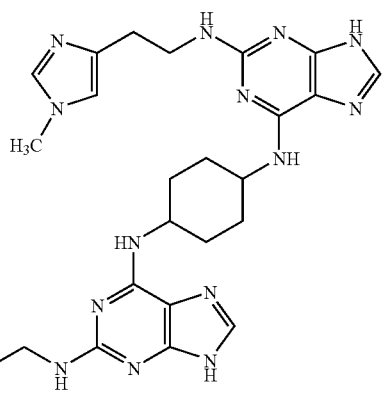
(V)

with a compound of formula (IV) as defined hereinabove or a protected derivative thereof. This reaction may be carried out in the presence of a hindered base such as DBU and a Lewis acid such as trimethylsilyl triflate.

A compound of formula (V) may be prepared by deprotecting a compound of formula (VI)

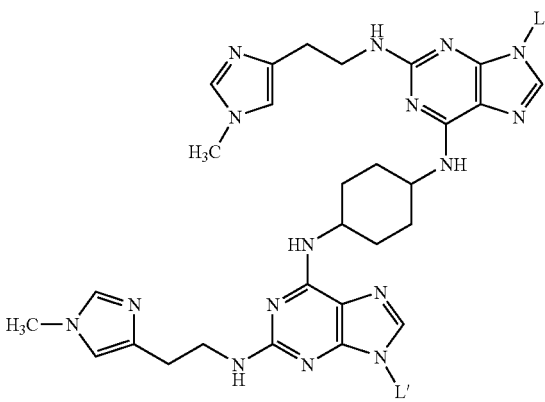
(VI)

wherein L' is a suitable amine protecting group such as 2-tetrahydropyran. Deprotection may typically be achieved by acid hydrolysis with a suitable acid such as HCl at ambient temperature.

A compound of formula (VI) may be prepared by reacting a compound of formula (VII)

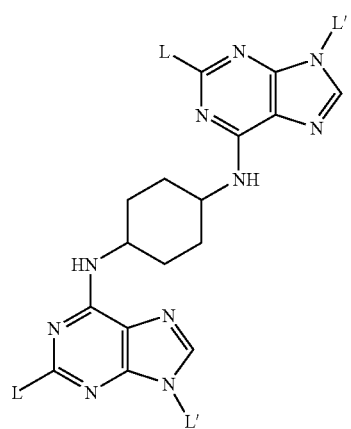
(VII)

wherein L and L' are as defined above, with [2-(1-methyl-1H-imidazolyl-4-yl)ethyl amine. Said reaction will generally involve heating the reagents to a temperature of 50° C. to 150° C., such as 100° C. to 130° C. particularly about 110° C. to 120° C., in the presence of an inert solvent such as DMSO or ethylene glycol. An external base such as dipotassium hydrogen phosphate can also be used to enhance the reactivity.

A compound of formula (VII) may be prepared by reacting a compound of Formula (VIII)

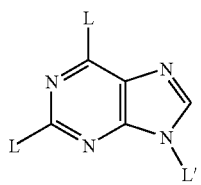

(VIII)

wherein L and L' are leaving groups as defined above with 1,4-diaminocyclohexane, such as trans-1,4-diaminocyclohexane. This reaction will generally be performed in the presence of a base such as an amine base (e.g. diisopropyl ethylamine in a suitable solvent such as an alcohol eg. isopropanol or n-butanol) at an elevated temperature (eg. 60° C. to 80° C.).

Compounds of formula (VII) may be prepared according to the methods described in WO03/080613 or by analogous methods. A compound of formula (VII) is Intermediate 1 in WO03/080613.

Compounds of formula (I) may further be prepared according to a third process (C) by deprotecting a protected derivative of a compound of formula (I), for example where the hydroxyl groups on the sugar moiety are protected by acetyl groups.

As described above protected derivatives of compounds of the invention or intermediates for preparing compounds of the invention may be used. Examples of protecting groups and the means for their removal can be found in T W Greene and P G M Wuts "Protective Groups in Organic Synthesis" (J Wiley and Sons, 1991). Suitable hydroxyl protecting groups include alkyl (eg. methyl), acetal (eg. acetonide) and acyl (eg. acetyl or benzoyl) which may be removed by hydrolysis, and arylalkyl (eg. benzyl) which may be removed by catalytic hydrogenolysis. Suitable amine protecting groups include sulphonyl (eg. tosyl), acyl eg. benzyloxycarbonyl or t-butoxycarbonyl) and arylalkyl (eg. benzyl) which may be removed by hydrolysis or hydrogenolysis as appropriate.

The potential for compounds of formula (I) and salts or solvates thereof to inhibit leukocyte function may be demonstrated, for example, by their ability to inhibit superoxide ($O_2^-$) generation from neutrophils stimulated with chemoattractants such as N-formylmethionyl-leucyl-phenylalanine (fMLP). Accordingly, compounds of formula (I) may be of potential therapeutic benefit in providing protection from leukocyte-induced tissue damage in diseases where leukocytes are implicated at the site of inflammation.

Examples of disease states in which compounds that inhibit leukocyte function may have potentially beneficial anti-inflammatory effects include diseases of the respiratory tract such as adult respiratory distress syndrome (ARDS), bronchitis (including chronic bronchitis), cystic fibrosis, asthma (including allergen-induced asthmatic reactions), emphysema, rhinitis and septic shock. Other relevant disease states include diseases of the gastrointestinal tract such as intestinal inflammatory diseases including inflammatory bowel disease (e.g. Crohn's disease or ulcerative colitis), *Helicobacter-pylori* induced gastritis and intestinal inflammatory diseases secondary to radiation exposure or allergen exposure, and non-steroidal anti-inflammatory drug-induced gastropathy. Further diseases may include skin diseases such as psoriasis, allergic dermatitis and hypersensitivity reactions and diseases of the central nervous system which have an inflammatory component e.g. Alzheimer's disease and multiple sclerosis.

Further examples of disease states in which such compounds may have potentially beneficial effects include cardiac conditions such as peripheral vascular disease, post-ischaemic reperfusion injury and idiopathic hypereosinophilic syndrome.

Yet further, compounds which inhibit lymphocyte function may be useful as immunosuppressive agents and so have use in the treatment of auto-immune diseases such as rheumatoid arthritis and diabetes, and may be useful in inhibiting metastasis.

It will be appreciated by those skilled in the art that reference herein to treatment extends to prophylaxis as well as the treatment of established conditions.

Of particular interest is the treatment and/or prophylaxis of asthma, chronic pulmonary obstructive disease (COPD), chronic bronchitis and emphysemia in a mammal (e.g. human) especially asthma and COPD.

As mentioned above, compounds of formula (I) and salts and solvates thereof may be useful in human or veterinary medicine, in particular as anti-inflammatory agents.

There is thus provided as a further aspect of the invention a compound of formula (I) or a pharmaceutically acceptable salt or solvate thereof for use in human or veterinary medicine, particularly in the treatment of patients with inflammatory conditions who are susceptible to leukocyte-induced tissue damage.

According to another aspect of the invention, there is provided the use of a compound of formula (I) or a pharmaceutically acceptable salt or solvate thereof for the manufacture of a medicament for the treatment of patients with inflammatory conditions who are susceptible to leukocyte-induced tissue damage.

In a further or alternative aspect there is provided a method for the treatment of a human or animal subject with an inflammatory condition and/or allergic condition who is susceptible to leukocyte-induced tissue damage, which method comprises administering to said human or animal subject an effective amount of a compound of formula (I) or a pharmaceutically acceptable salt or solvate thereof.

For use in medicine, compounds of the present invention are usually administered as a pharmaceutical composition.

The present invention therefore provides in a further aspect a pharmaceutical composition comprising a compound of formula (I) or a pharmaceutically acceptable salt or solvate therof optionally with one or more pharmaceutically acceptable carriers and/or excipients.

The pharmaceutical composition can be for use in the treatment and/or prophylaxis of any of the conditions described herein.

Compounds of formula (I) and salts and solvates thereof and/or the pharmaceutical composition containing them may be administered, for example, by parenteral (eg. intravenous, subcutaneous, or intramuscular), inhaled, nasal, transdermal or rectal administration, or as topical treatments (eg. ointments or gels). Routes of administration of particular interest include inhaled and intra-nasal. Inhaled administration involves topical administration to the lung, eg. by aerosol or dry powder composition.

The compound of formula (I) and salts and solvates thereof and/or the pharmaceutical composition may be administered by a controlled or sustained release formulation as described in WO 00/50011.

A parenteral composition can comprise a solution or suspension of the compound or pharmaceutically acceptable salt in a sterile aqueous carrier or parenterally acceptable oil. Alternatively, the solution can be lyophilised; the lyophilised parenteral pharmaceutical composition can be reconstituted with a suitable solvent just prior to administration.

Compositions for nasal or inhaled administration may conveniently be formulated as aerosols, solutions, suspensions, drops, gels or dry powders, with aqueous or non-aqueous vehicles optionally with the addition of agents such as thickening agents, buffer salts or acid or alkali to adjust the pH, isotonicity adjusting agents, antioxidants and/or preservatives.

Capsules and cartridges of for example gelatine, or blisters of for example laminated aluminium foil, for use in an inhaler or insufflator may be formulated containing a powder mix of a compound of the invention and a suitable powder base such as lactose or starch.

There is also provided a process for preparing such a pharmaceutical formulation which comprises mixing the ingredients.

For compositions suitable and/or adapted for inhaled administration, the compound or salt or solvate of formula (I) is typically in a particle-size-reduced form, and particularly the size-reduced form is obtained or obtainable by micronisation. Generally, the particle size of the size-reduced (e.g. micronised) compound or salt can be defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a chlorofluorocarbon (CFC) or hydrofluorocarbon (HFC). Suitable CFC propellants include dichlorodifluoromethane, trichlorofluoromethane and dichlorotetrafluoroethane. Suitable HFC propellants include 1,1,1,2,3,3,3-heptafluoropropane and 1,1,1,2-tetrafluoroethane. The aerosol dosage forms can also take the form of a pump-atomiser.

Optionally, in particular for dry powder inhalable compositions, a pharmaceutical composition for inhaled administration can be incorporated into a plurality of sealed dose containers (e.g. containing the dry powder composition) mounted longitudinally in a strip or ribbon inside a suitable inhalation device. The container is rupturable or peel-openable on demand and the dose of e.g. the dry powder composition can be administered by inhalation via the device such as the DISKUS™ device, marketed by GlaxoSmithKline. The DISKUS™ inhalation device is for example described in GB 2242134 A, and in such a device at least one container for the pharmaceutical composition in powder form (the container or containers preferably being a plurality of sealed dose containers mounted longitudinally in a strip or ribbon) is defined between two members peelably secured to one another; the device comprises: a means of defining an opening station for the said container or containers; a means for peeling the members apart at the opening station to open the container; and an outlet, communicating with the opened container, through which a user can inhale the pharmaceutical composition in powder form from the opened container.

The proportion of the active compound of formula (I) or salt or solvate thereof in the topical compositions according to the invention depends on the precise type of formulation to be prepared but may generally be within the range of from 0.001 to 10% by weight. Generally, however for most types of preparations the proportion used may be within the range of from 0.005 to 1% such as 0.01 to 0.5%. However, in powders for inhalation or insufflation the proportion used may be within the range of from 0.1 to 5%.

Aerosol formulations are preferably arranged so that each metered dose or "puff" of aerosol contains 20 μg-2000 μg, preferably about 20 μg-500 μg of a compound of formula (I). Administration may be once daily or several times daily, for example 2, 3, 4 or 8 times, giving for example 1, 2 or 3 doses each time. The overall daily dose with an aerosol will be within the range 100 μg-10 mg preferably, 200 μg-2000 μg. The overall daily dose and the metered dose delivered by capsules and cartridges in an inhaler or insufflator will generally be double those with aerosol formulations.

The compound (or salts and solvates thereof) and pharmaceutical formulations according to the invention may be used in combination with or include one or more other therapeutic agents, for example selected from anti-inflammatory agents, anticholinergic agents (particularly an $M_1$, $M_2$, $M_1/M_2$ or $M_3$ receptor antagonist), $\beta_2$-adrenoreceptor agonists, antiinfective agents (e.g. antibiotics, antivirals), or antihistamines. The invention thus provides, in a further aspect, a combination comprising a compound of formula (I) or a pharmaceutically acceptable salt, solvate or physiologically functional derivative thereof together with one or more other therapeutically active agents, for example selected from an anti-inflammatory agent (for example a corticosteroid or an NSAID), an anticholinergic agent, a $\beta_2$-adrenoreceptor agonist, an antiinfective agent (e.g. an antibiotic or an antiviral), or an antihistamine. Particular combinations of the invention include a compound of formula (I) or a physiologically acceptable salt or solvate thereof together with a steroid, a β₂-adrenoreceptor agonist, an anticholinergic, and/or a PDE-4 inhibitor. Preferred combinations are those comprising one or two other therapeutic agents.

It will be clear to a person skilled in the art that, where appropriate, the other therapeutic ingredient(s) may be used in the form of salts, (e.g. as alkali metal or amine salts or as acid addition salts), or prodrugs, or as esters (e.g. lower alkyl esters), or as solvates (e.g. hydrates) to optimise the activity and/or stability and/or physical characteristics (e.g. solubility) of the therapeutic ingredient. It will be clear also that where appropriate, the therapeutic ingredients may be used in optically pure form.

The invention thus provides, in a further aspect, a combination comprising a compound of formula (I) or a pharmaceutically acceptable salt or solvate thereof with one or more other therapeutically active agents, for example, a β₂-adrenoreceptor agonist, an anti-histamine, an anti-allergic agent, an anti-inflammatory agent (including a steroid or a PDE-4 inhibitor), an anticholinergic agent or an antiinfective agent (eg. antibiotics or antivirals).

Examples of β₂-adrenoreceptor agonists include salmeterol (which may be a racemate or a single enantiomer, such as the R-enantiomer), salbutamol, formoterol, salmefamol, fenoterol or terbutaline and salts thereof, for example the xinafoate salt of salmeterol, the sulphate salt or free base of salbutamol or the fumarate salt of formoterol. Long-acting β₂-adrenoreceptor agonists such as salmeterol or formoterol may be preferred.

Other long acting β₂-adrenoreceptor agonists include those described in WO02/66422A, WO02/270490, WO02/076933, WO03/024439, WO03/072539, WO 03/091204, WO04/016578, WO04/022547, WO041037807, WO04/037773, WO04/037768, WO04/039762, WO04/039766, WO01/42193 and WO03/042160.

Particular long-acting β₂-adrenoreceptor agonists are:
3-(4-{[6-({(2R)-2-hydroxy-2-[4-hydroxy-3-(hydroxymethyl)phenyl]ethyl}amino) hexyl]oxy}butyl)benzenesulfonamide;
3-(3-{[7-({(2R)-2-hydroxy-2-[4-hydroxy-3-hydroxymethyl)phenyl]ethyl}-amino)heptyl]oxy}propyl)benzenesulfonamide;
4-{(1R)-2-[(6-{2-[(2,6-dichlorobenzyl)oxy]ethoxy}hexyl)amino]-1-hydroxyethyl}-2-(hydroxymethyl)phenol;
4-{(1R)-2-[(6-{4-[3-(cyclopentylsulfonyl)phenyl]butoxy}hexyl)amino]-1-hydroxyethyl}-2-(hydroxymethyl)phenol;
N-[2-hydroxyl-5-[(1R)-1-hydroxy-2-[[2-4-[[(2R)-2-hydroxy-2-phenylethyl]amino]phenyl]ethyl]amino]ethyl]phenyl]formamide, and
N-2{2-[4-(3-phenyl-4-methoxyphenyl)aminophenyl]ethyl}-2-hydroxy-2-(8-hydroxy-2(1H) -quinolinon-5-yl)ethylamine.

Anti-inflammatory agents that may be incorporated in a combination include corticosteroids particularly inhaled corticosteroids and their pro-drugs which have anti-inflammatory activity. Examples of corticosteroids include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, 6α,9α-difluoro-11β-hydroxy-16α-methyl-17α-(1-methylcylopropylcarbonyl)oxy-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethylcyclopropylcarbonyl)oxy-androsta-1,4-diene-17β-carboxylic acid cyanomethyl ester, beclomethasone esters (such as the 17-propionate ester or the 17,21-dipropionate ester), budesonide, flunisolide, mometasone esters (such as the furoate ester), triamcinolone acetonide, rofleponide, ciclesonide, (16α,17-[[(R)-cyclohexylmethylene]bis (oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Non-steroidal compounds that may have glucocorticoid activity include those covered in the following patent applications WO03/082827, WO01/10143, WO98/54159, WO04/005229, WO04/009016, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277.

Anti-inflammatory agents include non-steroidal anti-inflammatory drugs (NSAID's).

Possible NSAID's that may be used in a combination include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example, montelukast), iNOS inhibitors, tryptase and elastase inhibitors, beta-2 integrin antagonists and adenosine receptor agonists or antagonists (for example, adenosine 2a agonists), cytokine antagonists (for example, chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Other iNOS inhibitors include those disclosed in WO93/13055, WO98/30537, WO02/50021, WO95/34534 and WO99/62875. Suitable CCR3 inhibitors include those disclosed in WO02/26722.

Phosphodiesterase 4 (PDE4) inhibitors that may be used in a combination include any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Another compound of interest is cis-4- cyano-4-[3-(cyclopentyloxy)-4-methoxyphenyl] cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other PDE4 inhibitors include AWD-12-281 from Elbion (Hofgen, N. et al. 15th EFMC Int Symp Med Chem (Sep. 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), PCT/EP20031014867 (Glaxo Group Ltd) and PCT/EP2004/005494 (Glaxo Group Ltd).

Anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS 136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (for example, CAS 28797-61-7), darifenacin (for example, CAS 133099-04-4, or CAS 133099-07-7 for the hydrobromide sold under the name Enablex), oxybutynin (for example, CAS 5633-20-5, sold under the name Ditropan), terodiline (for example, CAS 15793-40-5), tolterodine (for example, CAS 124937-51-5, or CAS 124937-52-6 for the tartrate, sold under the name Detrol), otilonium (for example, as the bromide, CAS 26095-59-0, sold under the name Spasmomen), trospium chloride (for example, CAS 10405-02-4) and solifenacin (for example, CAS 242478-37-1, or CAS 242478-38-2, or the succinate also known as YM-905 and sold under the name Vesicare).

Other anticholinergic agents include compounds of formula (XXI), which are disclosed in U.S. patent application No. 60/487981:

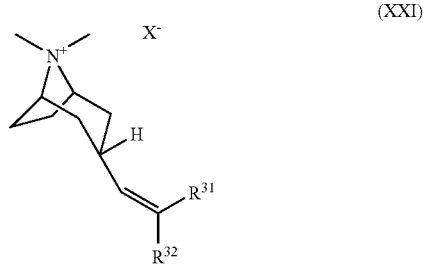

(XXI)

in which the preferred orientation of the alkyl chain attached to the tropane ring is endo;

$R^{31}$ and $R^{32}$ are, independently, selected from the group consisting of straight or branched chain lower alkyl groups having preferably from 1 to 6 carbon atoms, cycloalkyl groups having from 5 to 6 carbon atoms, cycloalkyl-alkyl having 6 to 10 carbon atoms, 2-thienyl, 2-pyridyl, phenyl, phenyl substituted with an alkyl group having not in excess of 4 carbon atoms and phenyl substituted with an alkoxy group having not in excess of 4 carbon atoms;

$X^-$ represents an anion associated with the positive charge of the N atom. $X^-$ may be but is not limited to chloride, bromide, iodide, sulfate, benzene sulfonate, and toluene sulfonate, including, for example:

(3-endo)-3-(2,2-di-2-thienylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane bromide;

(3-endo)-3-(2,2-diphenylethenyl)-8,8-dimethyl-8-azoniabicyclo[3.2.1]octane 4-methylbenzenesulfonate;

(3-endo)-8,8--dimethyl-3-[2-phenyl-2-(2-thienyl)ethenyl]-8-azoniabicyclo[3.2.1]octane bromide; and/or (3-endo)-8,8--dimethyl-3-[2-phenyl-2-(2-pyridinyl)ethenyl]-8-azoniabicyclo[3.2.1]octane bromide.

Further anticholinergic agents include compounds of formula (XXII) or (XXIII), which are disclosed in U.S. patent application 60/511009:

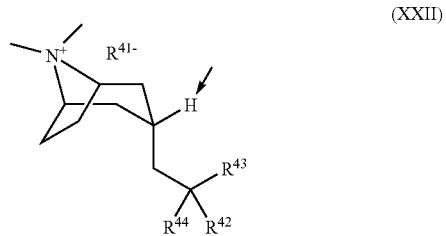

(XXII)

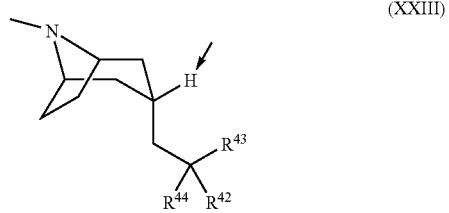

(XXIII)

wherein:

the H atom indicated is in the exo position;

$R^{41-}$ represents an anion associated with the positive charge of the N atom. $R1^-$ may be but is not limited to chloride, bromide, iodide, sulfate, benzene sulfonate and toluene sulfonate;

$R^{42}$ and $R^{43}$ are independently selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl;

$R^{44}$ is slected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, $-OR^{45}$, $-CH_2OR^{45}$, $-CH_2OH$, $-CN$, $-CF_3$, $-CH_2O(CO)R^{46}$, $-CO_2R^{47}$, $-CH_2NH_2$, $-CH_2N(R^{47})SO_2R^{45}$, $-SO_2N(R^{47})(R^{48})$, $-CON(R^{47})(R^{48})$, $-CH_2N(R^{48})CO(R^{46})$, $-CH_2N(R^{48})SO_2(R^{46})$, $-CH_2N(R^{48})CO_2(R^{45})$, $-CH_2N(R^{48})CONH(R^{47})$;

$R^{45}$ is selected from the group consisting of $(C_1-C_6)$alkyl, $(C_1-C_6)$alkyl$(C_3-C_{12})$cycloalkyl, $(C_1-C_8)$alkyl$(C_3-C_7)$heterocycloalkyl, $(C_1-C_6)$alkyl-aryl, $(C_1-C_6)$alkyl-heteroaryl;

$R^{46}$ is selected from the group consisting of $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl;

$R^{47}$ and $R^{48}$ are, independently, selected from the group consisting of H, $(C_1-C_6)$alkyl, $(C_3-C_{12})$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, and $(C_1-C_6)$alkyl-heteroaryl, including, for example:

(Endo)-3-(2-methoxy-2,2-di-thiophen-2-yl-ethyl)-8,8-dimethyl-8-azonia-bicyclo[3.2.1]octane iodide;
3-((Endo)-8-methyl-8-aza-bicyclo[3.2.1]oct-3-yl)-2,2-diphenyl-propionitrile;
(Endo)-8-methyl-3-(2,2,2-triphenyl-ethyl)-8-aza-bicyclo[3.2.1]octane;
3-((Endo)-8-methyl-8-aza-bicyclo[3.2.1]oct-3-yl)-2,2-diphenyl-propionamide;
3-((Endo)-8-methyl-8-aza-bicyclo[3.2.1]oct-3-yl)-2,2-diphenyl-propionic acid;
(Endo)-3-(2-cyano-2,2-diphenyl-ethyl)-8,8--dimethyl-8-azonia-bicyclo[3.2.1]octane iodide;
(Endo)-3-(2-cyano-2,2-diphenyl-ethyl)-8,8--dimethyl-8-azonia-bicyclo[3.2.1]octane bromide;
3-((Endo)-8-methyl-8-aza-bicyclo[3.2.1]oct-3-yl)-2,2-diphenyl-propan-1-ol;
N-Benzyl-3-((endo)-8-methyl-8-aza-bicyclo[3.2.1]oct-3-yl)-2,2-diphenyl-propionamide;
(Endo)-3-(2-carbamoyl-2,2-diphenyl-ethyl)-8,8--dimethyl-8-azonia-bicyclo[3.2.1]octane iodide;
1-Benzyl-3-[3-((endo)-8-methyl-8-aza-bicyclo[3.2.1]oct-3-yl)-2,2-diphenyl-propyl]-urea;
1-Ethyl-3-[3-((endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-acetamide;
N-[3-((Endo)-8-methyl-8-aza-bicyclo[3.2.1]oct-3-yl)-2,2-diphenyl-propyl]-benzamide;
3-((Endo)-8-methyl-8-aza-bicyclo[3.2.1]oct-3-yl)-2,2-di-thiophen-2-yl-propionitrile;
(Endo)-3-(2-cyano-2,2-di-thiophen-2-yl-ethyl)-8,8-dimethyl-8-azonia-bicyclo[3.2.1]octane iodide;
N-[3-((Endo)-8-methyl-8-aza-bicyclo[3.2.1]oct-3-yl)-2,2-diphenyl-propyl]-benzenesulfonamide;
[3-((Endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-methanesulfonamide; and/or
(Endo)-3-{2,2-diphenyl-3-[(1-phenyl-methanoyl)-amino]-propyl}-8,8-dimethyl-8-azonia-bicyclo[3.2.1]octane bromide.

More preferred compounds useful in the present invention include:
(Endo)-3-(2-methoxy-2,2-di-thiophen-2-yl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane iodide;
(Endo)-3-(2-cyano-2,2-diphenyl-ethyl)-8,8-dimethyl-8-azonia-bicyclo[3.2.1]octane bromide;
(Endo)-3-(2-carbamoyl-2,2-diphenyl-ethyl)-8,8-dimethyl-8-azonia-bicyclo[3.2.1]octane iodide;
(Endo)-3-(2-cyano-2,2-di-thiophen-2-yl-ethyl)-8,8-dimethyl-8-azonia-bicyclo[3.2.1]octane iodide; and/or
(Endo)-3-{2,2-diphenyl-3-[(1-phenyl-methanoyl)-amino]-propyl}-8,8-dimethyl-8-azonia-bicyclo[3.2.1]octane bromide.

Antihistamines (also referred to as H1-receptor antagonists) include any one or more of the numerous antagonists known which inhibit H1-receptors, and are safe for human use. First generation antagonists, include derivatives of ethanolamines, ethylenediamines, and alkylamines, such as diphenylhydramine, pyrilamine, clemastine, chlorpheniramine. Second generation antagonists, which are non-sedating, include loratidine, desloratidine, terfenadine, astemizole, acrivastine, azelastine, levocetirizine fexofenadine, cetirizine and efletirizine.

The invention thus provides, in a further aspect, a combination comprising a compound of formula (I) or a pharmaceutically acceptable salt or solvate thereof together with a PDE4 inhibitor.

The invention thus provides, in a further aspect, a combination comprising a compound of formula (I) or a pharmaceutically acceptable salt or solvate thereof together with a $\beta_2$-adrenoreceptor agonist.

The invention thus provides, in a further aspect, a combination comprising a compound of formula (I) or a pharmaceutically acceptable salt or solvate thereof together with an anticholinergic.

The invention thus provides, in a further aspect, a combination comprising a compound of formula (I) or a pharmaceutically acceptable salt or solvate thereof together with an antihistamine.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

The individual compounds of such combinations may be administered either sequentially or simultaneously in separate or combined pharmaceutical formulations. Preferably, the individual compounds will be administered simultaneously in a combined pharmaceutical formulation. Appropriate doses of known therapeutic agents will be readily appreciated by those skilled in the art.

The compounds of formula (I) and salts and solvates thereof may be prepared by the methodology described hereinafter, constituting a further aspect of this invention.

The combinations referred to above may conveniently be presented for use in the form of a pharmaceutical composition and thus a pharmaceutical composition comprising a combination as defined above optionally together with one or more pharmaceutically acceptable carriers and/or excipients represent a further aspect of the invention.

The individual compounds of such combinations may be administered either sequentially or simultaneously in separate or in combined pharmaceutical compositions.

Intermediate compounds described herein may form a further aspect of the invention.

The compounds of the invention may have one or more of the following advantageous properties: more efficacious; show greater selectivity; have fewer side effects; have a longer duration of action; be more bioavailable by the preferred route; show less systemic activity when administered by inhalation; and/or have other more desirable properties than similar known compounds.

In particular the compounds of the invention may be highly potent at the $A_{2A}$ receptor, show greater selectivity for the $A_{2A}$ receptor subtype over other adenosine receptor subtypes (especially the $A_1$ and $A_3$ receptor subtypes), capable of being highly bound to human serum albumin (greater than about 90%, particularly greater than about 95%), and/or may exhibit less pronounced cardiac effects that hitherto known compounds.

Compounds of the invention may be tested for in vitro and in vivo biological activity in accordance with the following or similar assays/models.

1) In Vitro: Agonist Activity Against Adenosine $A_1$, $A_{2A}$, $A_{2B}$ and $A_3$ Receptors.

The agonist potency and selectivity of compounds against human adenosine receptors is determined using Chinese hamster ovary (CHO) cells or yeast cells transfected with the gene for the relevant receptor.

(a) CHO Cells

Two methods may be used in the CHO cells. (i) For the SPAP assay, cells are also transfected with cyclic AMP (cAMP) response elements promoting the gene for secreted placental alkaline phosphatase (SPAP). Changes in cAMP are measured as changes in the levels of SPAP. (ii) The DiscoveRx assay is an enzyme complementation assay that involves two fragments of β-galactosidase, enzyme acceptor (EA) and enzyme donor (ED). Following the production of cAMP EA binds to ED, active enzyme is produced and a luminescent product is formed following the addition of substrate. For both methods the effect of test compounds is determined by their effects on basal levels of cAMP ($A_{2A}$ and $A_{2B}$) or on forskolin enhanced cAMP ($A_1$ and $A_3$).

(b) Yeast Cells

For the yeast assay, receptor stimulation causes activation of a reporter gene, namely FUS1-HIS3, resulting in histidine production which is essential for cell growth. Yeast cells are cultured in growth medium lacking histidine, and addition of a test compound causes histidine production which in turn stimulates cell growth. This response is measured from the production of the exoglucanase, an enzyme secreted constitutively by yeast cells.

In all of the in vitro assays the activity of test compounds is expressed as a ratio to that of the non-selective adenosine receptor agonist, N-ethyl carboxamide adenosine (NECA).

In these or similar assays the formate salt of the compound of formula (I) was shown to be highly selective—being greater than 100 fold more selective for $A_{2A}$ than $A_1$, $A_{2B}$ and $A_3$. Potency at $A_{2A}$ was <0.5 (EMR vs NECA), and generally about 0.02 (EMR vs NECA).

In Vivo Anti-Inflammatory Agonist Activity

LPS Model:

Test compound was administered to male CD albino rats prior to exposure to LPS. Compound (or vehicle) was injected in a 200 ul volume into the trachea, via a cannula placed trans-orally, whilst the animals were under isoflurane anaesthesia. After a recovery period of 30 min, rats were placed in a chamber and exposed to an aerosol of *E. Coli*-derived LPS for 15 min. Four hours after LPS challenge the rats were killed, the lungs lavaged, and both total and differential cell counts determined. The dose of test compound giving a 50% reduction in neutrophil accumulation (ED50) was determined.

In this or a similar assay the formate salt of the compound of formula (I) gave greater than 50% reduction in neutrophil accumulation at a dose of 30 μg/kg or less.

3) Therapeutic Index (TI)

Cardiovascular Model:

Male Wistar rats were anaesthetised with chloralose/pentobarbitone and the jugular vein, left carotid artery and trachea were cannulated. The arterial cannula was connected to a transducer for the continuous measurement of blood pressure and heart rate. Compound (or vehicle) was administered into the trachea in a 100 ul volume, and the dose of test compound giving a 20% increase in blood pressure and heart rate (ED20) was determined.

The TI for a test compound is calculated as the ratio of the ED20 in the cardiovascular model compared with the ED50 in the LPS model.

The dose so determined for the formate salt of the compound of formula (I) in this or a similar model was about 7 μg/kg.

(4) HSA Binding

Instrument: Agilent HP1100 HPLC instruments were used throughout.

HPLC columns: Chromtech Immobilised HSA HPLC column 50×3 mm was purchased from Chromtech (Cheshire, UK).

Mobile phase and detection: The mobile phase A was 50 mM pH 7.4 ammonium acetate solution, while mobile phase B was 2-Propanol (HPLC grade, Runcorn, UK). The mobile phase flow rate was 1.8 ml/min. The column temperature was kept at 30° C. The gradient profile and run time were the same with each column, the linear gradient from 0 to 30% 2-propanol was applied from 0 to 3 minutes. From 3 to 10 minutes, the mobile phase composition was constant 30% 2-propanol and 70% 50-mM ammonium acetate. From 10 min to 10.5 min the mobile phase composition was change to 100% ammonium acetate buffer only and remained the same until the end of the run. Each separation was stopped after 15 minutes.

Detection: Chromatograms were recorded at 230 and 254 nm by a diode array UV absorption detector at room temperature.

Calibration of the protein columns: The column performance check and the calibration have been performed before the analysis of every 96 well plate. The compounds used for the column calibrations were dissolved separately in 0.5 mg/ml concentration in 50% 2-propanol and 50% pH 7.4 ammonium acetate solution mixtures. The calibration set of compounds their literature % plasma protein binding and its linear conversion value (logK lit), as well as typical retention times, their logarithmic values, log K derived from the calibration curve and % binding data are listed in Table 1.

TABLE 1

Calibration set of compounds with their literature and typical measured chromatographic data obtained with the HSA column.
(Literature data were obtained from ref. 16.)

| Compound | Literature % PPB | tR | logtR | lit logK | logK measured | % HSA measured |
|---|---|---|---|---|---|---|
| Warfarin2 | 98 | 4.393 | 0.64 | 1.51 | 1.53 | 98.1 |
| Nizatidine | 35 | 0.6 | −0.22 | −0.28 | −0.35 | 31.1 |
| Bromazepam | 60 | 1.299 | 0.11 | 0.17 | 0.38 | 71.2 |
| Carbamazepine | 75 | 1.48 | 0.17 | 0.46 | 0.50 | 76.8 |
| Budesonide | 88 | 1.826 | 0.26 | 0.83 | 0.70 | 84.2 |
| Piroxicam | 94.5 | 2.787 | 0.45 | 1.16 | 1.10 | 93.6 |
| Nicardipine | 95 | 3.768 | 0.58 | 1.20 | 1.38 | 97.0 |
| Ketoprofen | 98.7 | 3.916 | 0.59 | 1.63 | 1.42 | 97.3 |
| Indomethacin | 99 | 6.023 | 0.78 | 1.69 | 1.83 | 99.5 |
| Diclofenac | 99.8 | 5.94 | 0.77 | 1.92 | 1.81 | 99.5 |

The literature % PPB (bound in plasma) values were converted to the linear free energy related logk values (logarithm of apparent affinity constant) using the following equation.

$$\mathrm{Log}\, K = \log\left[\frac{\%\, PPB}{(101 - \%\, PPB)}\right] - [\mathrm{Plasma\ Protein}]$$

The formate salt of the compound of formula (I) in this or a similar assay showed greater than about 90% binding to HSA.

The various aspects of the invention will now be described by reference to the following Examples. These Examples are merely illustrative and are not to be construed as a limitation of the scope of the present invention.

General Experimental Details

All reactions were carried out under an atmosphere of nitrogen unless specified otherwise All temperatures are given in degrees centigrade.

Where products were purified by column chromatography, 'flash silica' refers to silica gel for chromatography, 0.035 to 0.070 mm (220 to 440 mesh) (e.g. Fluka silica gel 60), where column elution was accelerated by an applied pressure of nitrogen at up to 10 p.s.i.

Where thin layer chromatography (TLC) has been used, it refers to silica gel TLC using plates typically 4×10 cm silica gel on aluminium foil plates with a fluorescent indicator (254 nm), (e.g. Fluka 60778). Biotage refers to prepacked silica gel caRTridges containing KP-Sil run on flash 12i chromatography module. Solid Phase Extraction (SPE) columns are prepacked caRTridges used in parallel purifications, normally under vacuum. These are commercially available from Varian. SCX caRTridges are Ion Exchange SPE columns where the stationary phase is polymeric benzene sulfonic acid. These are used to isolate amines.

The $H^1$-nmr spectra were recorded on a Bruker AV400 400 operating at 400 MHz or a Bruker DPX-250 operating at 250 MHz. $D_6$-DMSO was used as solvent unless stated otherwise. Tetramethylsilane was used as internal standard.

LC/MS Systems

The Liquid Chromatography Mass Spectroscopy (LC/MS) systems used:

LCMS System : LCMS was conducted on a Supelcosil LCABZ+PLUS column (3.3 cm×4.6 mm ID) eluting with 0.1% $HCO_2H$ and 0.01M ammonium acetate in water (solvent A) and 0.05% $HCO_2H$ 5% water in acetonitrile (solvent B), using the following elution gradient 0.0-7 min 0% B, 0.7-4.2 min 100% B, 4.2-5.3 min 100% B, 5.3-5.5 min 0% B at a flow rate of 3 mL/min. The mass spectra were recorded on a Fisons VG Platform spectrometer using electro spray positive and negative mode (ES+ve and ES−ve).

Preparative HPLC Conditions

Where products were purified by preparative HPLC, this was carried out on a C18-reverse-phase column (10×2.1 cm i.d. Genesis column with 7 μm particle size), eluting first isocratically with 10% acetonitrile phase then with a gradient of acetonitrile (containing 0.1% trifluoroacetic acid) in water (containing 0.1% trifluoroacetic acid) at a flow rate of 5 ml/min. The gradient was started at 10% acetonitrile and was increased at a rate of 1% per minute. UV detection at 230 nm was used unless otherwise stated.

Mass Directed Auto Prep (MDAP) HPLC Conditions

Preparative mass directed HPLC was conducted on a Waters FractionLynx system comprising of a Waters 600 pump with extended pump heads, Waters 2700 autosampler, Waters 996 diode array and Gilson 202 fraction collector on a 10 cm×2.54 cm ill ABZ+ column, eluting with 0.1% formic acid in water (solvent A) and 0.1% formic acid in acetonitrile (solvent B), using the following elution gradient: 0.0-1.0 min 15% B, 1.0-10.0 min 55% B, 10.0-14.5 min 99% B, 14.5-14.9 min 99% B, 14.9-15.0 min 15% B at a flow rate of 20 ml/min and detecting at 200-320 nm at room temperature. Mass spectra were recorded on Micromass ZMD mass spectrometer using electro spray positive and negative mode, alternate scans. The software used was MassLyn.x 3.5 with OpenLynx and FractionLynx options.

XRPD analysis of certain salts was carried out according to the following or similar methodology.

| | |
|---|---|
| Manufacturer | PANalytical - The Netherlands |
| Instrument | X'Pert Pro |
| Diffractometer Type | DY1850 |
| Tube anode | Cu |
| K-Alpha1 wavelength (A°) | 1.54056 |
| K-Alpha2 wavelength (A°) | 1.54439 |
| Ration Alpha 1:2 | 0.50000 |
| Divergence slit | Prog.Div.Slit |
| Receiving slit | Prog.Rec.Slit |
| Generator voltage (kV) | 40 |
| Tube Current (mA) | 45 |
| Detector | X'celerator |
| Data Angle range (°2θ) | 2.000-40.000 |
| Scan type | Continuous |
| Scan step size | 0.0167 |
| Scan step time (seconds) | 31.75 |
| Sample preparation | Flush Silicon wafer |

XRPD analysis was performed on a PANalytical X'Pert Pro X-ray powder diffractometer, model X'Pert Pro PW3040/60, serial number DY1850 using an X'Celerator detector. The acquisition conditions were: radiation: Cu K, generator tension: 40 kV, generator current: 45 mA, start angle: 2.000°2θ, end angle: 40.000°2θ, step size: 0.0167, time per step: 31.75 seconds. The sample was prepared using flush Silicon wafer.

Abbreviations Used in the Experimental Section
IPA=isopropanol
DCM=dichloromethane
THF=tetrahydofuran
MeOH=methanol
DMF=dimethylformamide
DIPEA=di-isopropylethylamine
EtOAc=ethyl acetate
ACN=acetonitrile
CHC=cyclohexane
DMSO=dimethylsulphoxide
RT=room temperature
DMAP=4-dimethylaminopyridine
HATU=O-(7-Azabenzotriazol-1-yl)-N,N,N',N'-tetramethyluronium hexafluorophosphate.
NBS=N-bromosuccinimde
IMS=industrial methylated spirit
TFA=trifluoroacetic acid
Boc=teRTiary.butyloxycarbonyl
$R_t$=retention time
h: hour(s)
min: minute(s)
Flash silica gel refers to Merck ART No. 9385; silica gel refers to Merck ART No. 7734

Intermediate 1

Trans-1,4-cyclohexanediylbis[imino(2-chloro-9H-purine-6,9-diyl)(2R,3R,4R,5R)-5-(2-ethyl-2H-tetrazol-5-yl)tetrahydrofuran-2,3,4-triyl]tetraacetate

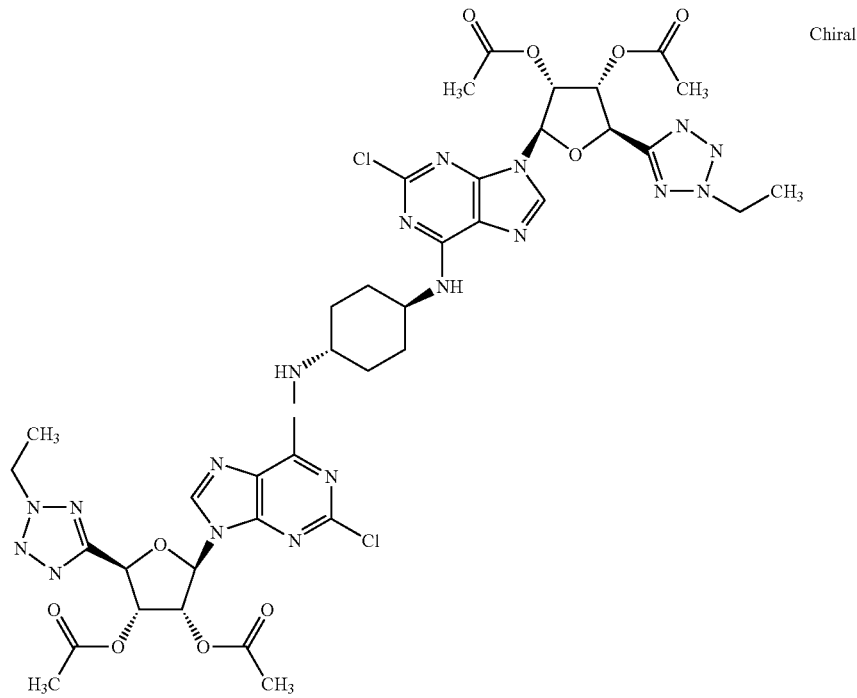

A mixture of (2R,3R,4R,5R)-2-(2,6-dichloro-9h-purin-9-yl)-5-(2-ethyl-2h-tetrazol-5-yl)tetrahydrofuran-3,4-diyl diacetate (Intermediate 7 in WO98/28319), (2.36 g, 5 mmol), trans-1,4- diaminocyclohexane (630 mg, 5.5 mmol) and DIPEA (0.960 mL) in IPA (30 mL) was stirred and heated at 60° C. for 19.5 h. After cooling solvent was removed in vacuo. Crude reaction mixture was purified on Flash Silica Isolute cartridge (50 g) eluted in a gradient from cyclohexane through to cyclohexane/ethyl acetate (1:3 to 1:1) to neat ethylacetate. Appropriate fractions were combined and upon removal of solvent in vacuo, the title compound was obtained as a white solid (1.46 g).

LC/MS $R_t$ 3.58 min m/z 983 [MH]$^+$

Intermediate 2

Trans-N,N'-bis[2-chloro-9-(tetrahydro-2H-pyran-2-yl)-9H-purin-6-yl]-1,4-cyclohexanediamine

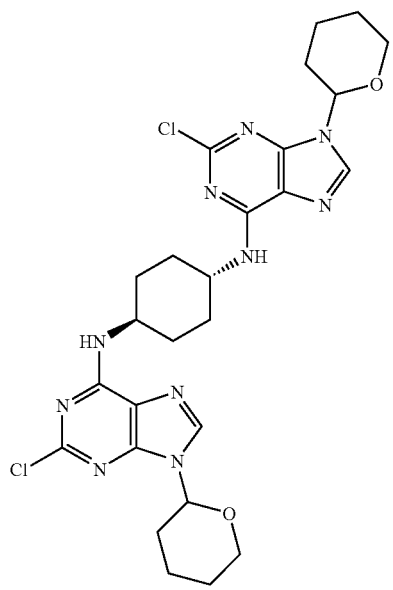

A stirred suspension of 2,6-dichloro-9-(tetrahydro-2H-pyran-2-yl)-9H-purine (Intermediate 1 in WO03/080613) (17 g; 62.3 mmoles) in isopropanol (500 ml) was treated with trans-1,4-diaminocyclohexane (3.6 g; 31.5 mmoles) and diisopropylethylamine (15 ml) was heated at 75° C. for 6 hours.

Additional trans-1,4-diaminocyclohexane (0.9 g; 7.9 mmoles) was added and heating was continued for a further 16 hours. A further portion of trans-1,4-diaminocyclohexane (0.9 g; 7.9 mmoles) was added and heating was continued for a further 7 hours at 85° C. The suspension was allowed to cool to ambient temperature and was allowed to stand. The solid was filtered off and was washed with iso-propanol followed by ether then was sucked dry. The solid (18.5 g) was partitioned between ethyl acetate and saturated aqueous sodium bicarbonate solution. The aqueous phase and solid was separated and was extracted with ethylacetate. Undissolved solid was filtered and partitioned between chloroform and saturated sodium bicarbonate solution. The combined organic extracts were dried over sodium sulphate and the solvent was evaporated. The resultant foam was suspended in ethyl acetate to give a solid. The solvent was evaporated and the residue was triturated with ether to give a solid which was filtered off, was washed with ether and was dried to provide the title compound as a white solid (16.3 g).

LC/MS $R_t$ 3.33 min m/z 587,589[MH]$^+$

Intermediate 3

N$^6$,N$^{6'}$-trans-1,4-cyclohexanediylbis[N$^2$-[2-(1-methyl-1H-imidazol-4-yl)ethyl]-9-(tetrahydro-2H-pyran-2-yl)-9H-purine-2,6-diamine]

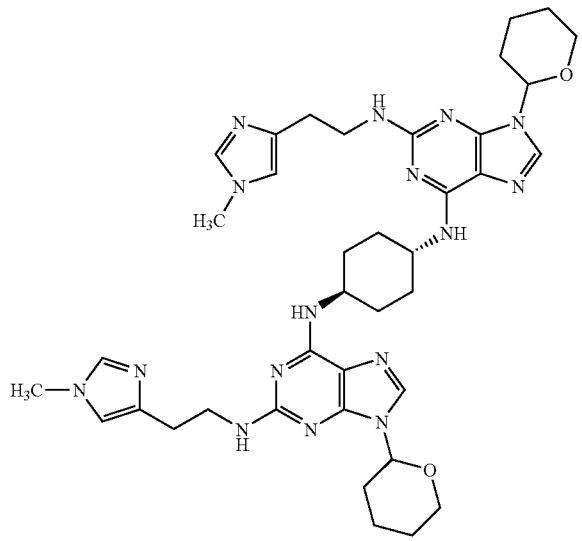

A mixture of Intermediate 2 (10 g; 17.0 mmoles) and N-methylhistamine (25.4 g; from 100 g bistosylate, 203 mmoles) in anhydrous dimethylsulphoxide (20 ml) was heated at 115° C. for 24 hours. The dark solution was allowed to cool to ambient temperature then was diluted slowly with water (400 ml) followed by ethyl acetate (75 ml). The mixture was stirred vigorously until the sticky lumps had solidified and broken up. The solid was filtered off, was washed with water and was dried to give the title compound (12.2 g).

LC/MS $R_t$ 2.08 min m/z 383[(M+2H)/2]$^+$, 765[MH]$^+$

Intermediate 4

N$^6$,N$^{6'}$-trans-1,4-cyclohexanediylbis{N$^2$-[2-(1-methyl-1H-imidazol-4-yl)ethyl]-3H-purine-2,6-diamine}

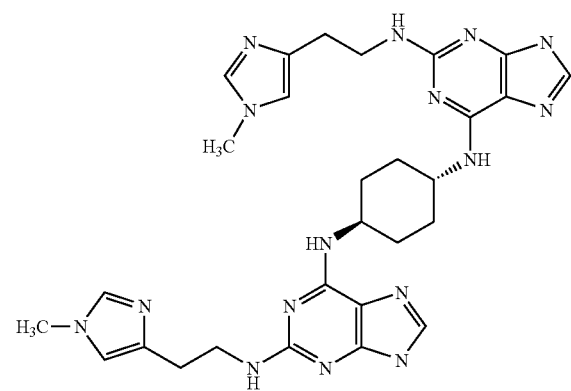

A solution of Intermediate 3 (11.8 g; 15.4 mmoles) in methanol (100 ml) was treated with 2M hydrochloric acid (25 ml) and was stirred at ambient temperature for 4 hours. The mixture was concentrated to remove methanol then was diluted with water (50 ml). Saturated aqueous sodium bicarbonate solution (70 ml) was added and the mixture was stirred for 1 hour. The solid was filtered off and was washed with water and dried. The solid was stirred with water for 15 mins. Suspension was mixed with chloroform and water. Methanol was added and the mixture was shaken. The mixture was concentrated in vacuo, methanol was added and evaporated. This was done three times to furnish a solid. The solid was titurated with ether filtered off and dried in vacuo at 35° C. to give the title compound (8.2 g).

LC/MS $R_t$ 1.73 min m/z 299 [(M+2H)/2]$^+$, 597 [MH]$^+$

Intermediate 5

Trans-1,4-cyclohexanediylbis[imino(2-{[2-(1-methyl-1H-imidazol-4-yl)ethyl]amino}-9H-purine-6,9-diyl)(2R,3R,4R,5R)-5-(2-ethyl-2H-tetrazol-5-yl)tetrahydrofuran-2,3,4-triyl]tetraacetate A suspension of Intermediate 4 (5.5 g; 9.22 mmoles) in ethyl acetate (50 ml) was treated with a solution of rel-Acetic acid 4R,5-diacetoxy-2R-(2-ethyl-2H-tetrazol-5-yl)-tetrahydrofuran-3R-yl ester (Intermediate 6 of WO98/28319), (11.4 g, 33.2 mmoles) in ethyl acetate (50 ml) and was cooled to 0° C. DBU (3.54 ml; 23.6 mmoles) was added followed by trimethylsilyl triflate (15.4 ml; 92.9 mmoles). The reaction was stirred at ambient temperature for 4.5 hours then was heated at 50° C. for 3 hours. The reaction was allowed to cool then was left standing overnight. Water was added followed by saturated aqueous sodium bicarbonate solution. After stirring three phases were obtained. The aqueous phase and oil were separated and were extracted with chloroform (×3). The combined organic extracts (chloroform and ethylacetate) were dried over sodium sulphate and the solvent was evaporated. The residue was chromatographed down a column of silica (Merck ART 9385 600 ml) eluted with chloroform (400 ml) followed by chloroform/methanol/0.88 aqueous ammonia solution (95:5:0.4). Appropriate fractions were combined and the solvent was evaporated to give the title compound (9.5 g, 4.2 g of 90% pure product approximately).

LC/MS $R_t$ 2.33 min m/z 581 [(M+2H)/2]$^+$

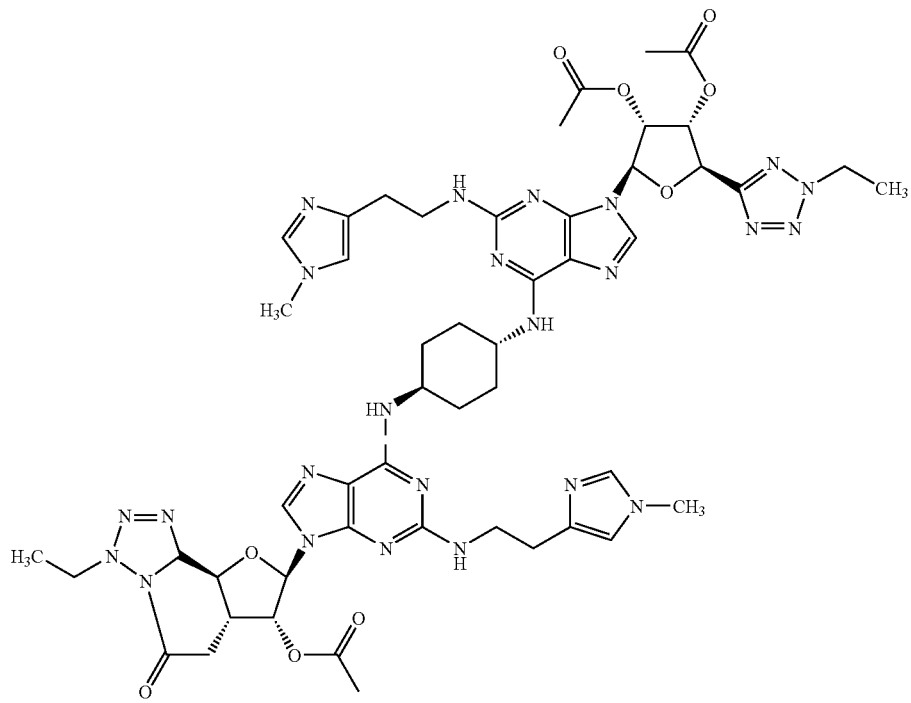

EXAMPLE 1

Formic acid—(2R,3R,4S,5R,2'R,3'R,4'S,5'R)-2,2'-{trans-1,4-cyclohexanediylbis[imino(2-{[2-(1-methyl-1H-imidazol-4-yl)ethyl]amino}-9H-purine-6,9-diyl)]}bis[5-(2-ethyl-2H-tetrazol-5-yl)tetrahydro-3,4-furandiol] (4:1)

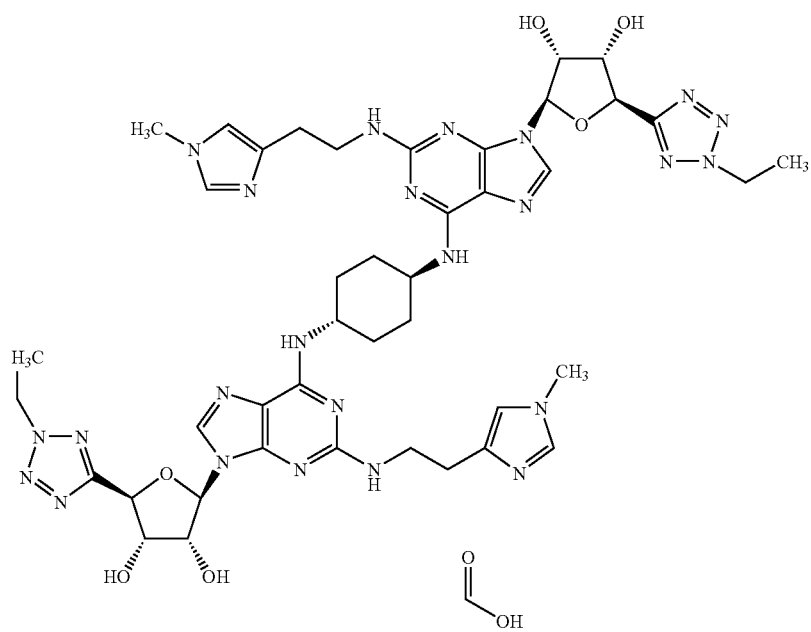

[2-(1-methyl-1H-imidazol-4-yl)ethyl]amine (763 mg, 6.1 mM) was added to Intermediate 1 (300 mg, 0.31 mM) dissolved in anhydrous DMSO (5 ml) and the solution was stirred under nitrogen at 120° C. for 21 h. and then allowed to cool. Water (20 ml) was added and precipitate was filtered off, which was purified by mass-directed autoprep HPLC. Appropriate fractions were combined and evaporated to afford the title compound (36 mg) as an off-white solid.

MDAP LC/MS $R_t$ 2.39 min m/z 993.7[MH]$^+$ $^1$Hnmr: 250 MHz$^+$

| Shift (ppm) | Multiplicity | Integral |
| --- | --- | --- |
| 8.15 | s | 2H |
| 7.80 | s br | 2H |
| 7.40 | s | 2H |

-continued

| Shift (ppm) | Multiplicity | Integral |
| --- | --- | --- |
| 6.80 | s | 2H |
| 6.30 | s br | 2H |
| 6.00 | d | 2H |
| 5.85 | s br | 2H |
| 5.20 | d | 2H |
| 4.82 | m | 4H |
| 4.68 | q | 4H |
| 4.18 | s br | 2H |
| 3.60 | s | 6H |
| 3.52 | t br | 4H |
| 2.78 | t | 4H |
| 2.08 | d br | 4H |
| 1.54 | t + m | 10H |

EXAMPLE 2

(2R,3R,4S,5R,2'R,3'R,4'S,5'R)-2,2'-{trans-1,4-cyclo-hexanediylbis[imino(2-{[2-(1-methyl-1H-imidazol-4-yl)ethyl]amino}-9H-purine-6,9-diyl)]}bis[5-(2-ethyl-2H-tetrazol-5-yl)tetrahydro-3,4-furandiol]

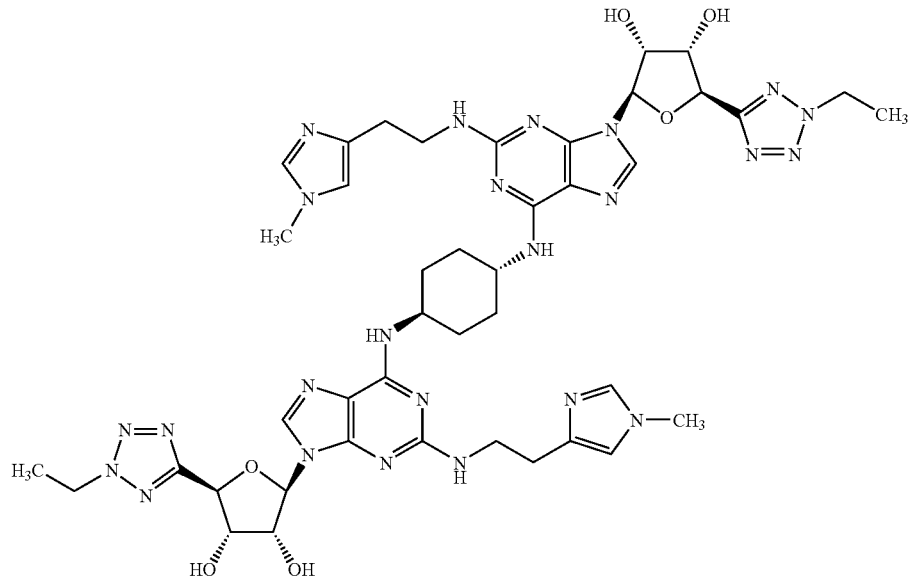

A solution of Intermediate 5 (18.1 g; 15.6 mmoles) in methanol (150 ml) was treated with sodium methoxide (1 g; 18.5 mmoles). After 30 minutes Dowex 50 [H$^+$] was added to neutralise the solution and additional methanol (100 ml) was added. The resin was filtered off and the filtrate was evaporated to leave the title compound as a foam/gum (13.3 g).

LC/MS R$_t$ 2.06 min m/z 497 [(M+2H)/2]$^+$.

$^1$Hnmr: 400 MHz

| Shift (ppm) | Multiplicity | Integral |
|---|---|---|
| 8.31 | s | 2H |
| 7.92 | s br | 2H |
| 7.47 | s | 2H |
| 7.08 | s br | 2H |
| 6.90 | s | 2H |
| 6.55 | s br | 2H |
| 5.95 | d | 2H |
| 5.70 | s br | 2H |
| 5.11 | d | 2H |
| 4.79 | s br | 2H |
| 4.66 | q | 4H |
| 4.04 | s br | 2H |
| 3.58 | s | 6H |
| 3.41 | m | 4H |
| 2.72 | t | 4H |
| 1.92 | s br | 4H |
| 1.46 | t + m | 10H |

Salt Preparation

Mono Maleate Hydrate Salt

Compound as free base (300 mg) was dissolved in ethanol (4.4 ml, 14.7 vols) at 75° C. Maleic acid (35.9 mg, 1.05 equivs) was dissolved in ethanol (1 ml, 3.3 vols) at room temperature. The maleic acid solution was added portion wise to the compound/ethanol solution with seeding with heating to 75° C. as appropriate. The resulting suspension was aged at 75° C. for 30 mins before cooling to room temperature over 2 hours and then aged at room temperature for a further hour. The product was isolated by filtration, washed with ethanol (1 ml) and dried at room temperature overnight under vacuum. The yield was 84.9%. The XRPD trace is shown in FIG. 1.

Mono Terephthlate Salt

Compound as free base (300 mg) and terephthalic acid (49.2 mg, 1.05 equivs) were suspended in ethanol (5.4 ml, 18 vols). The suspension was heated to 75° C. for 30 mins, then cooled to 40° C. and left to temperature cycle between 0-40° C. overnight with magnetic stirring. The product was isolated by filtration, washed with ethanol (3×2 ml) and dried at 60° C. overnight under vacuum. The yield was 71.3%. The XRPD trace is shown in FIG. 2.

In an alternative method the terephthlate salt was prepared as follows:

The compound as free base (1 g) was suspended in ethanol (80 ml, 80 vols) and was heated at 80° C. to form a solution. The terephthalic acid (123 mg, 1.05 eq) was then added to the solution portion wise over a period of 7 hours. The suspension was then cooled to room temperature for two days with magnetic stirring and was then left at room temperature for 3 days without any magnetic stirrer. The product was isolated by filtration, washed with ethanol (3×5 ml) and dried overnight under vacuum. The yield was 55%.

Mono Phthalate Salt

Compound as free base (300 mg) and phthalic acid (49.2 mg, 1.05 equivs) were suspended in ethanol (5.4 ml, 18 vols). The suspension was heated to 75° C. for 30 mins, where it virtually formed a solution. The reaction mixture was cooled to 40° C. and left to temperature cycle between 0-40° C. overnight with magnetic stirring. The product was isolated by filtration, washed with ethanol (2×2 ml) and dried at 60° C. overnight under vacuum. The yield was 80.0%. The XRPD trace is shown in FIG. 3.

Seeds may be produced by conventional methods using the desired acid (for example, maleic acid, hydrochloric acid, terephthalic acid, and phthalic acid) and by the methods described herein. The resultant seeds may then be used in subsequent salt preparations of typically the same salt but may also be used in the preparation of different salts, to improve the crystallinity of the salt product.

EXAMPLE 3

Further Preparations of (2R,3R,4S,5R,2'R,3'R,4'S,5'R)-2,2'-{trans-1,4-cyclohexanediylbis[imino(2-{[2-(1-methyl-1H-imidazol-4-yl)ethyl]amino}-9H-purine-6,9-diyl)]}bis[5-(2-ethyl-2H-tetrazol-5-yl)tetrahydro-3,4-furandiol] by Process A Stage 1:

Acetic acid, 4R-acetoxy-2R-(2,6-dichloro-purin-9-yl)-5R-(2-ethyl-2H-tetrazol-5-yl)-tetrahydro-furan-3R-yl ester (Intermediate 7 of WO98/28319)

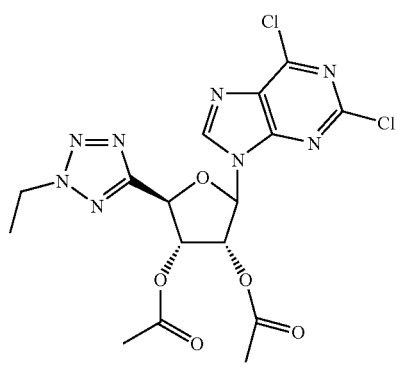

Trimethylsilyl trifluromethanesulfonate (200 g, 900.9 mmol) was added to a suspension of 2,6-dichloropurine (85.1 g, 450.5 mmol) in acetonitrile (850 ml) and stirred for 45 minutes. Then a solution of rel-Acetic acid 4R,5-diacetoxy-2R-(2-ethyl-2H-tetrazol-5-yl)-tetrahydro-furan-R-yl ester (Intermediate 6 of WO98/28319) (123.29, 360.4 mmol) in acetonitrile (510 ml) was added over 55 minutes. The mixture was stirred at ambient temperature overnight then quenched with water (200 ml) for 10 minutes and then saturated aqueous sodium bicarbonate (1.6 L). The acetonitrile was evaporated and the resulting aqueous was extracted with dichloromethane (2×400 ml). The combined organic extracts was washed with saturated aqueous sodium bicarbonate (200 ml), water (200 ml), dried over anhydrous sodium sulphate and evaporated to an oil. The oil was dissolved in IPA (1L) at 50° C., cooled to about 42° C. and seeded and sonicated. Cooling was continued to about 28° C. and the resultant mixture was aged at 38-40° C. for 30 mins. The mixture was cooled to about 25° C., filtered, washed with IPA (3×170 ml) and dried to give the title compound (111.5 g).

Stage 2:

Trans-1,4-cyclohexanediylbis[imino(2-chloro-9H-purine-6,9-diyl)(2R,3R,4R,5R)-5-(2-ethyl-2H-tetrazol-5-yl)tetrahydrofuran-2,3,4-triyl]tetraacetate (Intermediate 1)

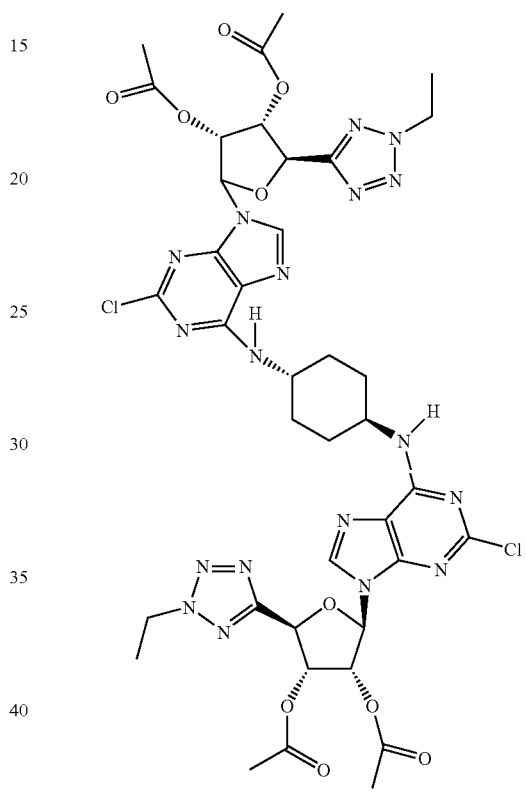

A mixture of Stage 1 (110.3 g, 234.2 mmol), 1,4-trans-diaminocylcohexane (16.02 g, 140.5 mmol), di-isopropylethylamine (122.2 ml, 702.6 mmol) and iso-propanol (550 ml) was heated at 82° C. for 20 hours. Extra 1,4-trans-diaminocylcohexane (0.8 g), di-isopropylethylamine (6.1 ml) was added and heating continued for another 24 hours. The mixture was cooled to 50° C., diluted with ethyl alcohol (250 ml) and heated at 50° C. for 1 hour. The slurry was then cooled to ambient temperature, filtered and washed with ethyl alcohol (250 ml). The wet cake was reslurried with ethyl alcohol (550 ml) at 78° C. for 1 hour, cooled to ambient temperature (about 30° C.), filtered and washed with ethyl alcohol (250 ml). The wet cake was reslurried with ethyl alcohol (550 ml) and water (110 ml) at 78° C. for 1 hour, cooled to ambient temperature, filtered, washed with 5:1 ethyl alcohol/water (240 ml) and ethyl alcohol (250 ml) then dried to give the title compound (77.9 g).

Stage 3:

(3R,4S,5R,3'R,4'S,5'R)-2,2'-{trans-cyclohexane-1,4-diylbis[imino(2-chloro-9H-purine-6,9-diyl)]}bis[5-(2-ethyl-2H-tetrazol-5-yl)tetrahydrofuran-3,4-diol]

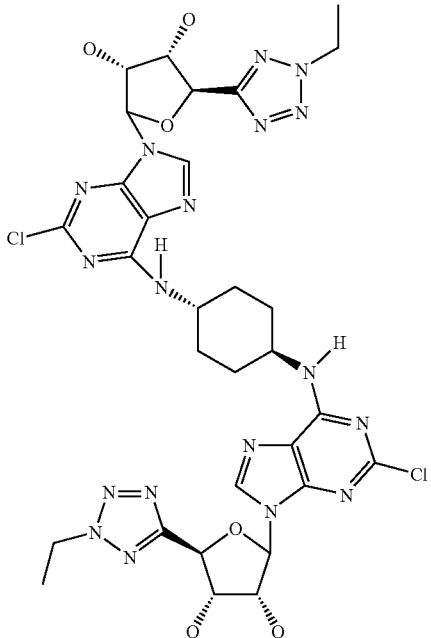

Sodium methoxide (0.63 g, 11.7 mmol) was added to a slurry of Stage 3 (77 g, 78.2 mmol) in methyl alcohol (770 ml) and stirred for 23 hours. The slurry was filtered, washed with methyl alcohol (380 ml) and dried to give the title compound (61.4 g).

$^1$H NMR (d$^6$-DMSO, 400 MHz) δ 1.45-1.68 (10H, m), 1.83-2.07 (4H, m), 4.03 (1.4H, br s)*, 4.54-4.59 (2H, m), 4.63 (0.6H, br s)*, 4.69-4.82 (6H, m), 5.22 (2H, d), 5.86 (4H, br s), 6.03-6.09 (2H, m), 8.26-8.37 (2H, m), 8.44 (1H, s), 8.46 (1H, s). * indicates non-whole integrals due to the presence of rotamers.

Stage 4:

(2R,3R,4S,5R,2'R,3'R,4'S,5'R)-2,2'-{trans-1,4-cyclohexanediylbis[imino(2-{[2-(1-methyl-1H-imidazol-4-yl)ethyl]amino}-9H-purine-6,9-diyl)]}bis[5-(2-ethyl-2H-tetrazol-5-yl)tetrahydro-3,4-furandiol] maleate hydrate salt

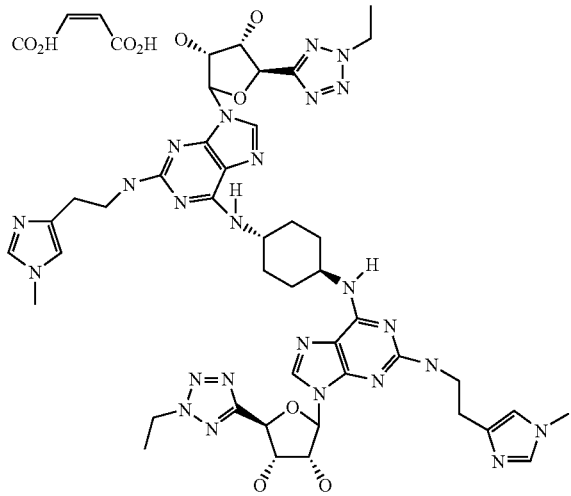

A mixture of Stage 3 (55 g, 67.4 mmol), N-methyl histamine (84.7 g, 674 mmol) and anhydrous dimethyl sulfoxide (138 ml) was heated at 100° C. for 16.5 hours. The mixture was cooled to ambient temperature then added over 45 minutes to water (1.4 L). The slurry was stirred for 45 minutes, filtered, washed with water (2×700 ml) and dried. The crude product (60 g), maleic acid (7 g) and methyl alcohol (360 ml) was heated at 65° C. for 90 minutes, cooled to 30° C. and seeded, then cooled to ambient temperature (20-25° C.) and stirred for 90 minutes. The slurry was filtered, washed with methyl alcohol (110 ml) and dried to give the title compound (39.2 g).

$^1$H NMR (d$^4$-MeOH, 400 MHz) δ 1.39-1.53 (4H, m), 1.6 (6H, t), 2.10-2.21 (4H, m), 2.92 (4H, t), 3.64 (4H, t), 3.71 (6H, s), 4.06 (2H, br s), 4.70 (4H, q), 4.80 (2H, br s), 4.89 (2 H, br s)*, 5.30 (2H, d), 6.09 (2H, d), 6.24 (2H, s), 7.08 (2H, s), 8.06 (2H, s), 8.08 (2H, s). * signal obscured by HOD

EXAMPLE 4

Further Preparation of (2R,3R,4S,5R,2'R,3'R,4'S,5'R)-2,2'-{trans-1,4-cyclohexanediylbis[imino(2-{[2-(1-methyl-1H-imidazol-4-yl)ethyl]amino}-9H-purine-6,9-diyl)]}bis[5-(2-ethyl-2H-tetrazol-5-yl)tetrahydro-3,4-furandiol] by Process B Stage 1:

Trans-N,N'-bis[2-chloro-9-(tetrahydro-2H-pyran-2-yl)-9H-purin-6-yl]-1,4-cyclohexanediamine (Intermediate 2)

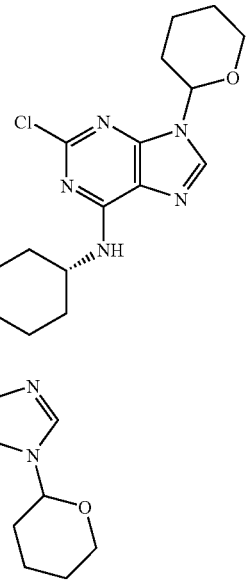

A stirred suspension of 2,6-dichloro-9-(tetrahydro-2H-pyran-2-yl)-9H-purine (Intermediate 1 in WO03/080613) (1.14 kg) in n-butanol (1.7 L) was treated with trans-1,4-diaminocyclohexane (239.2 g) and di-iso-propylethylamine (2.5 L), then heated at 75° C. for 17 hours. The suspension was allowed to cool to ambient temperature, filtered, washed with n-butanol (2×2.3 L) and dried in vacuo at 60° C. to give the title compound (0.9 kg).

Stage 2:

N⁶,N⁶'-trans-1,4-cyclohexanediylbis{N²-[2-(1-methyl-1H-imidazol-4-yl)ethyl]-3H-purine-2,6-diamine} (Intermediate 4)

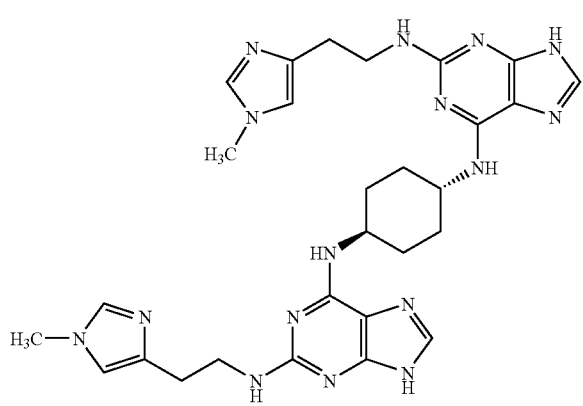

A mixture of Stage 1 (59.3 g; 100 mmol), N-methylhistamine (50.5 g; 400 mmoles), dipotassium hydrogen phosphate (35.1 g, 200 mmol) in ethylene glycol (60 ml) was heated at 120° C. for 8 days. The mixture was allowed to cool to ambient temperature then 5M aqueous hydrochloric acid (245 ml) is added with ice cooling for 50 minutes. Methanol (296 ml) was added followed by di-isopropylethylamine (246 ml) added dropwise over 30 minutes and the solution was heated to 60° C. for 1 hour. Water (178 ml) was slowly added at 60° C. over 30 minutes then stirred overnight at 25° C. The resulting slurry was heated to 60° C. and water (160 ml) was added dropwise. The slurry was cooled to ambient temperature, filtered, washed with water (120 ml), 1:2 methyl alcohol/water (120 ml), methyl alcohol (120 ml) and dried in vacuo at 40° C. to give a damp product (48.8 g). The damp product (40.8 g) was dried further in vacuo at 60° C. for 2 days to give the title compound (38.9 g).

Stage 3:

Trans-1,4-cyclohexanediylbis[imino(2-{[2-(1-methyl-1H-imidazol-4-yl)ethyl]amino}-9H-purine-6,9-diyl)(2R,3R,4R,5R)-5-(2-ethyl-2H-tetrazol-5-yl)tetrahydrofuran-2,3,4-triyl] tetraacetate (Intermediate 5)

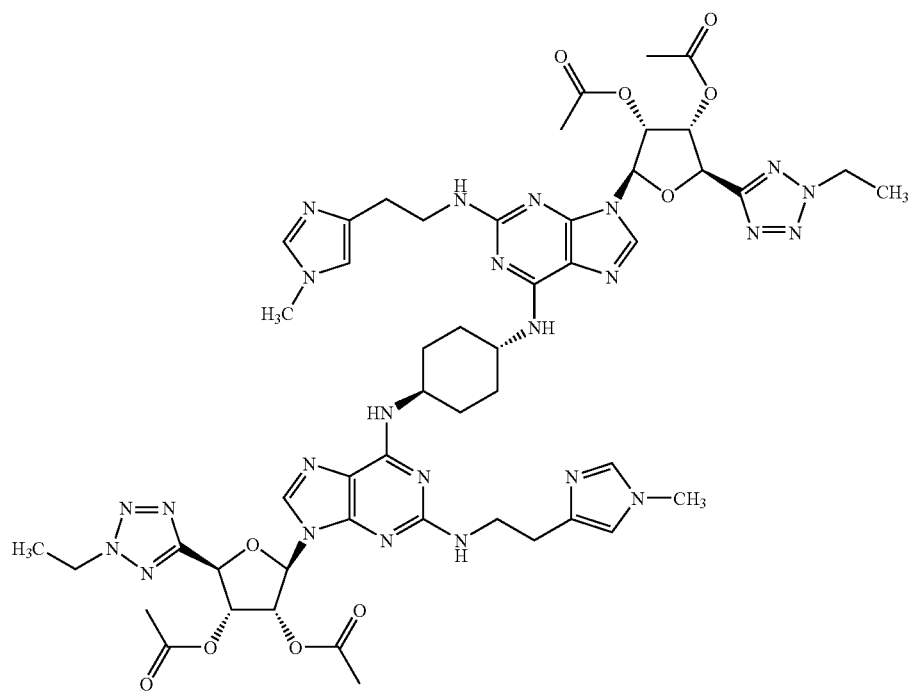

Trimethylsilyl trifluoromethanesulfonate (30.3 ml, 167 mmol) was added to a suspension of Stage 2 (20 g, 33.9 mmol) in acetonitrile (200 ml) then heated at 50° C. for 30 minutes. Then a solution of rel-Acetic acid 4R,5-diacetoxy- 2R-(2-ethyl-2H-tetrazol-5-yl)-tetrahydro-furan-3R-yl ester (Intermediate 6 of WO98/28319)(28.7 g, 84 mmol) in acetonitrile (200 ml) was added over 30 minutes and stirred for 20 hours. The reaction mixture was cooled to ambient temperature and quenched with water (50 ml) for 35 minutes then 5M aqueous hydrochloric acid (2×50 ml) for 90 minutes. The mixture was partitioned between dichloromethane (250 ml) and aqueous saturated sodium bicarbonate (700 ml) and the dichloromethane layer was allowed to stand at ambient temperature overnight. The organic portion was then extracted with 1M aqueous hydrochloric acid (2×300 ml). The acidic extracts were neutralised with aqueous saturated sodium bicarbonate (750 ml) then extracted with dichloromethane (2×200 ml). The combined dichloromethane extracts was washed with brine (100 ml), dried over anhydrous magnesium sulphate and concentrated to give the title compound (28.9 g) that was used without purification.

Stage 4:

(2R,3R,4S,5R,2'R,3'R,4'S,5'R)-2,2'-{trans-1,4-cyclohexanediylbis[imino(2-{[2-(1-methyl-1H-imidazol-4-yl)ethyl]amino}-9H-purine-6,9-diyl)]}bis[5-(2-ethyl-2H-tetrazol-5-yl)tetrahydro-3,4-furandiol]

1 hour. The mixture was cooled to ambient temperature (seeded at 40° C.) then stirred for overnight, filtered, washed with methanol (2×2 ml) and dried in vacuo at 55° C. The solid was further recrystallised (twice) from methanol (2×5 volumes) to give the maleate salt (0.6 g).

REFERENCES

Asako H, Wolf, R E, Granger, D N (1993), Gastroenterology 104, pp 31-37;
Bedford C D, Howd R A, Dailey O D, Miller A, Nolen H W III, Kenley R A, Kern J R, Winterle J S, (1986), J. Med. Chem. 29, pp 2174-2183;
Burkey T H, Webster, R O, (1993), Biochem. Biophys Acta 1175, pp 312-318;
Castanon M J, Spevak W, (1994), Biochem. Biophys Res. Commun. 198, pp 626-631;
Cronstein B N, Kramer S B, Weissmann G, Hirschhorn R, (1983), Trans. Assoc. Am. Physicians 96, pp 384-91;
Cronstein B N, Kramer S B, Rosenstein E D, Weissmann G, Hirschhorn R, (1985), Ann N.Y. Acad. Sci. 451, pp 291-301;
Cronstein B N, Naime D, Ostad E, (1993), J. Clin. Invest. 92, pp 2675-82;

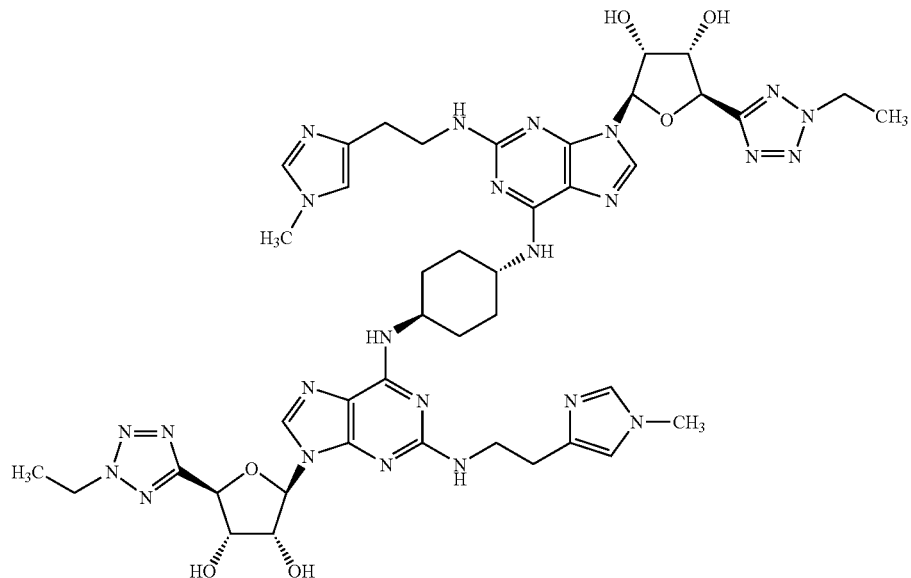

A solution of Stage 3 (28.6 g; assume 24.7 mmol) in methanol (515 ml) was treated with sodium methoxide (0.44 g, 8.13 mmol) for 90 minutes before being treated with a further portion of sodium methoxide (0.44 g, 8.13 mmol). After 30 minutes Dowex 50 [H+] was added to neutralise the solution. The resin was filtered off and the filtrate was evaporated to leave the title Compound as a foam (24 g).

Stage 5:

Mono Maleate Hydrate Salt

A solution of maleic acid (0.25 g, 2.11 mmol) in methanol (2 ml) was added to a solution of (2R,3R,4S,5R,2'R,3'R,4'S,5'R)-2,2'-{trans-1,4-cyclohexanediylbis[imino(2-{[2-(1-methyl-1H-imidazol-4-yl)ethyl]amino}-9H-purine-6,9-diyl)]}bis[5-(2-ethyl-2H-tetrazol-5-yl)tetrahydro-3,4-furandiol] (2 g, 2.01 mmol) in methanol (8 ml) at 65° C. and stirred for Cronstein B N, Naime D, Ostad E, (1994), Adv. Exp. Med. Biol., 370, pp 411-6;
Cronstein B N, (1994), J. Appl. Physiol. 76, pp 5-13;
Dianzani C, Brunelleschi S, Viano I, Fantozzi R, (1994), Eur. J. Pharmacol 263, pp 223-226;
Elliot K R F, Leonard E J, (1989), FEBS Letters 254, pp 94-98;
Flora K P, van't Riet B, Wampler G L, (1978), Cancer Research, 38, pp 1291-1295;
Green P G, Basbaum A I, Helms C, Levine J D, (1991), Proc. Natl. Acad Sci. 88, pp 4162-4165;
Hirschorn R, (1993), Pediatr. Res 33, pp S35-41;
Kohno Y; Xiao-duo J; Mawhorter S D; Koshiba M; Jacobson K A. (1996).Blood 88 p 3569-3574.
Peachell P T, Lichtenstein L M, Schleimer R P, (1989), Biochem Pharmacol 38, pp 1717-1725;

Richter J, (1992), J. Leukocyte Biol. 51, pp 270-275;
Rosengren S, Bong G W, Firestein G S, (1995), J. Immunol. 154, pp 5444-5451;
Sanjar S, McCabe P J, Fattah D, Humbles M, Pole S M, (1992), Am. Rev. Respir. Dis. 145, A40;
Skubitz K M, Wickman N W, Hammerschmidt D E, (1988), Blood 72, pp 29-33
Valko K, Nunhuck S, Bevan C, Abraham M C, Reynolds D P. (2003) J Pharm Sci 92 p 2236-2248.
Van Schaick E A; Jacobson K A; Kim H O; Ijzerman A P; Danhof M. (1996) Eur J Pharmacol 308 p 311-314.
Wood K V. (1995) Curr Opinion Biotechnology 6 p 50-58.

All publications, including but not limited to patents and patent applications, cited in this specification are herein incorporated by reference.

The invention claimed is:

1. A compound according to Formula (I):

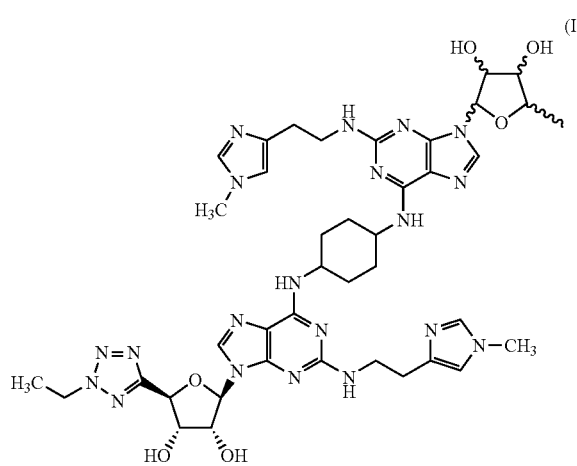

(I)

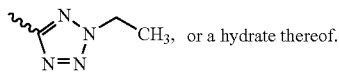

2. The compound according to claim 1, wherein the compound is present as a hydrate.

3. A pharmaceutical composition comprising a compound according to claim 2 and one or more pharmaceutically acceptable diluents or carriers.

4. A pharmaceutical composition comprising a compound according to claim 1 and one or more pharmaceutically acceptable diluents or carriers.

5. (2R,3R,4S,5R,2'R,3'S,4'S,5'R)-2,2'-{trans-1,4-cyclohexanediylbis[imino(2-{[2-(1-methyl-1H-imidazol-4-yl)ethyl]amimo}-9H-purine-6,9.diyl)]}bis[5-(2-ethyl-2-H-tetrazol-5-yl)tetrahydro-3,4-furandiol] or a hydrate thereof.

6. The compound according to claim 5, wherein the compound is present as a hydrate.

7. A pharmaceutical composition comprising the compound of claim 6 and one or more pharmaceutically acceptable diluents or carriers.

8. A pharmaceutical composition comprising the compound of claim 5 and one or more pharmaceutically acceptable diluents or carriers.

9. A pharmaceutically acceptable salt of a compound according to Formula (I):

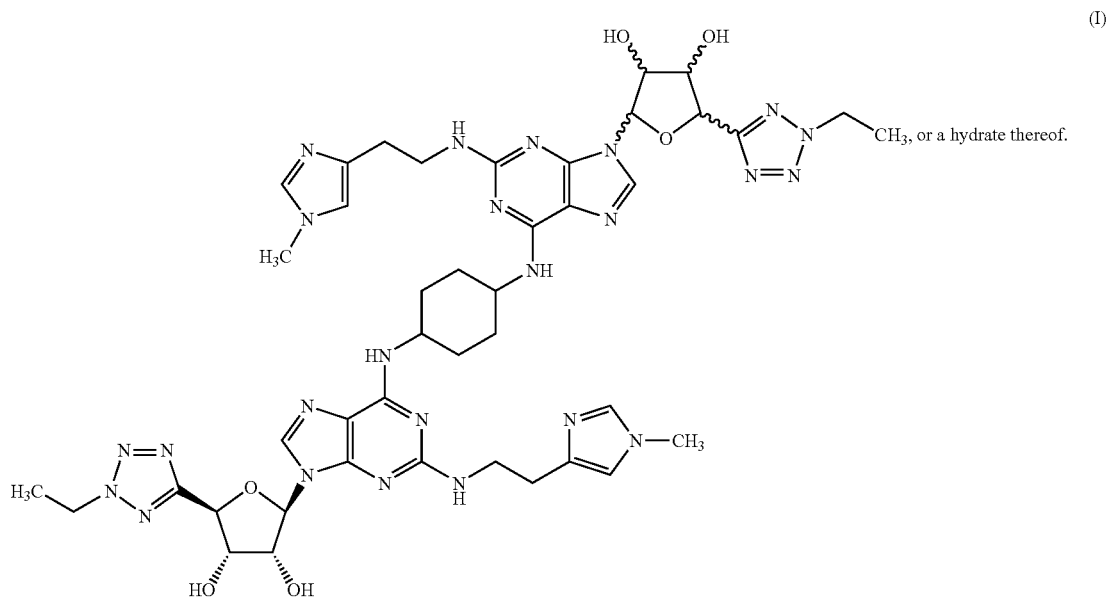

(I)

10. A pharmaceutical composition comprising the compound of claim 9 and one or more pharmaceutically acceptable diluents or carriers.

11. The pharmaceutically acceptable salt according to claim 9, wherein the salt is the maleate salt, and wherein the maleate salt is present as a hydrate.

12. A pharmaceutical composition comprising the compound of claim 11 and one or more pharmaceutically acceptable diluents or carriers.

13. (2R,3R,4S,5R,2'R,3'R,4'S,5'R)-2,2'-{trans-1,4-cyclohexanediylbis[imino(2-{[2-(1-methyl-1H-imidazol-4-yl)ethyl]amimo}-9H-purine-6,9-diyl)]}bis[5-(2-ethyl-2-H-tetrazol-5-yl)tetrahydro-3,4-furandiol] in the form of a pharmaceutically acceptable salt or a hydrate of said salt.

14. The pharmaceutically acceptable salt according to claim 13, wherein the salt is the maleate salt, and wherein the maleate salt is present as a hydrate.

15. A pharmaceutical composition comprising the compound of claim 14 and one or more pharmaceutically acceptable diluents or carriers.

16. A pharmaceutical composition comprising the compound of claim 13 and one or more pharmaceutically acceptable diluents or carriers.

17. A method of treating an inflammatory disease of the respiratory tract which comprises administering to a patient in need thereof an effective amount of a compound according to claim 1.

18. The method according to claim 17, wherein the inflammatory disease of the respiratory tract is asthma.

19. The method according claim 17, wherein the inflammatory disease of the respiratory tract is emphysema.

20. The method according to claim 17, wherein the inflammatory disease of the respiratory tract is chronic obstructive pulmonary disease (COPD).

21. The method according to claim 17, wherein the inflammatory disease of the respiratory tract is chronic bronchitis.

22. A method of treating an inflammatory disease of the respiratory tract which comprises administering to a patient in need thereof an effective amount of a compound according to claim 5.

23. The method according to claim 22, wherein the inflammatory disease of the respiratory tract is asthma.

24. The method according to claim 22, wherein the inflammatory disease of the respiratory tract is emphysema.

25. The method according to claim 22, wherein the inflammatory disease of the respiratory tract is chronic obstructive pulmonary disease (COPD).

26. The method according to claim 22, wherein the inflammatory disease of the respiratory tract is chronic bronchitis.

27. A method of treating an inflammatory disease of the respiratory tract which comprises administering to a patient in need thereof an effective amount of a compound according to claim 2.

28. The method according to claim 27, wherein the inflammatory disease of the respiratory tract is asthma.

29. The method according to claim 27, wherein the inflammatory disease of the respiratory tract is emphysema.

30. The method according to claim 27, wherein the inflammatory disease of the respiratory tract is chronic obstructive pulmonary disease (COPD).

31. The method according to claim 27, wherein the inflammatory disease of the respiratory tract is chronic bronchitis.

32. A method of treating an inflammatory disease of the respiratory tract which comprises administering to a patient in need thereof an effective amount of a compound according to claim 6.

33. The method according to claim 32, wherein the inflammatory disease of the respiratory tract is asthma.

34. The method according to claim 32, wherein the inflammatory disease of the respiratory tract is emphysema.

35. The method according to claim 32, wherein the inflammatory disease of the respiratory tract is chronic obstructive pulmonary disease (COPD).

36. The method according to claim 32, wherein the inflammatory disease of the respiratory tract is chronic bronchitis.

37. A method of treating an inflammatory disease of the respiratory tract which comprises administering to a patient in need thereof an effective amount of a compound of according to claim 9.

38. The method according to claim 37, wherein the inflammatory disease of the respiratory tract is asthma.

39. The method according to claim 37, wherein the inflammatory disease of the respiratory tract is emphysema.

40. The method according to claim 37, wherein the inflammatory disease of the respiratory tract is chronic obstructive pulmonary disease (COPD).

41. The method according to claim 37, wherein the inflammatory disease of the respiratory tract is chronic bronchitis.

42. A method of treating an inflammatory disease of the respiratory tract which comprises administering to a patient in need thereof an effective amount of a compound of according to claim 11.

43. The method according to claim 42, wherein the inflammatory disease of the respiratory tract is asthma.

44. The method according to claim 42, wherein the inflammatory disease of the respiratory tract is emphysema.

45. The method according to claim 42, wherein the inflammatory disease of the respiratory tract is chronic obstructive pulmonary disease (COPD).

46. The method according to claim 42, wherein the inflammatory disease of the respiratory tract is chronic bronchitis.

47. A method of treating an inflammatory disease of the respiratory tract which comprises administering to a patient in need thereof an effective amount of a compound of according to claim 13.

48. The method according to claim 47, wherein the inflammatory disease of the respiratory tract is asthma.

49. The method according to claim 47, wherein the inflammatory disease of the respiratory tract is emphysema.

50. The method according to claim 47, wherein the inflammatory disease of the respiratory tract is chronic obstructive pulmonary disease (COPD).

51. The method according to claim 47, wherein the inflammatory disease of the respiratory tract is chronic bronchitis.

52. A method of treating an inflammatory disease of the respiratory tract which comprises administering to a patient in need thereof an effective amount of a compound of according to claim 14.

53. The method according to claim 52, wherein the inflammatory disease of the respiratory tract is asthma.

54. The method according to claim 52, wherein the inflammatory disease of the respiratory tract is emphysema.

55. The method according to claim 52, wherein the inflammatory disease of the respiratory tract is chronic obstructive pulmonary disease (COPL)).

56. The method according to claim 52, wherein the inflammatory disease of the respiratory tract is chronic bronchitis.

\* \* \* \* \*